(12) United States Patent
Otte et al.

(10) Patent No.: US 8,039,230 B2
(45) Date of Patent: Oct. 18, 2011

(54) SELECTION OF HOST CELLS EXPRESSING PROTEIN AT HIGH LEVELS

(75) Inventors: Arie Pieter Otte, Amersfoort (NL); Henricus J. M. van Blokland, Wijdewormer (NL); Theodorus H. J. Kwaks, Amsterdam (NL); Richard G. A. B. Sewalt, Arnhem (NL)

(73) Assignee: Chromagenics B.V., Leiden (NL)

( * ) Notice: Subject to any disclaimer, the term of this patent is extended or adjusted under 35 U.S.C. 154(b) by 125 days.

(21) Appl. No.: 12/226,706

(22) PCT Filed: Apr. 24, 2007

(86) PCT No.: PCT/EP2007/053984
§ 371 (c)(1),
(2), (4) Date: Oct. 24, 2008

(87) PCT Pub. No.: WO2007/128685
PCT Pub. Date: Nov. 15, 2007

(65) Prior Publication Data
US 2009/0098601 A1    Apr. 16, 2009

(30) Foreign Application Priority Data
May 2, 2006  (EP) .................................. 06113354

(51) Int. Cl.
C12P 21/02   (2006.01)
C12N 1/21    (2006.01)
C12N 15/00   (2006.01)
C12N 15/09   (2006.01)
C12N 15/12   (2006.01)
C07H 21/04   (2006.01)

(52) U.S. Cl. ................. 435/69.1; 435/252.3; 435/320.1; 536/23.1

(58) Field of Classification Search ................. 435/69.1, 435/252.3, 320.1; 536/23.1
See application file for complete search history.

(56) References Cited

U.S. PATENT DOCUMENTS

| | | | |
|---|---|---|---|
| 4,965,196 A | 10/1990 | Levinson et al. | |
| 5,527,701 A | 6/1996 | Yamaguchi et al. | |
| 5,561,053 A | 10/1996 | Crowley | |
| 5,610,053 A | 3/1997 | Chung et al. | |
| 5,627,033 A | 5/1997 | Smith et al. | |
| 5,648,267 A * | 7/1997 | Reff | 435/320.1 |
| 5,733,779 A | 3/1998 | Reff | |
| 5,773,695 A | 6/1998 | Thompson et al. | |
| 5,888,809 A | 3/1999 | Allison | |
| 5,994,128 A | 11/1999 | Fallaux et al. | |
| 6,107,477 A | 8/2000 | Whitney et al. | |
| 6,319,707 B1 | 11/2001 | Adam et al. | |
| 6,395,549 B1 | 5/2002 | Tuan et al. | |
| 6,521,419 B1 | 2/2003 | Koduri et al. | |
| 6,558,948 B1 | 5/2003 | Kochanek et al. | |
| 6,586,205 B1 | 7/2003 | Glucksmann et al. | |
| 6,800,457 B2 | 10/2004 | Koduri et al. | |
| 6,872,524 B1 | 3/2005 | Otte | |
| 7,192,741 B2 | 3/2007 | Otte et al. | |
| 7,244,609 B2 * | 7/2007 | Drocourt et al. | 435/252.33 |
| 7,655,441 B2 | 2/2010 | Otte et al. | |
| 7,659,094 B2 | 2/2010 | Otte et al. | |
| 7,662,591 B2 | 2/2010 | Otte et al. | |
| 7,736,868 B2 | 6/2010 | Otte et al. | |
| 7,736,869 B2 | 6/2010 | Otte et al. | |
| 7,736,870 B2 | 6/2010 | Otte et al. | |
| 7,749,733 B2 | 7/2010 | Otte et al. | |
| 2002/0155540 A1 | 10/2002 | Padidam | |
| 2003/0138908 A1 | 7/2003 | Koduri et al. | |
| 2003/0166042 A1 | 9/2003 | Glucksmann et al. | |
| 2003/0199468 A1 | 10/2003 | Otte et al. | |
| 2004/0219677 A1 * | 11/2004 | Drocourt et al. | 435/488 |
| 2005/0106609 A1 | 5/2005 | Otte | |
| 2005/0181428 A1 | 8/2005 | Antoniou et al. | |
| 2005/0191723 A1 | 9/2005 | Otte et al. | |
| 2006/0003416 A1 | 1/2006 | Otte et al. | |
| 2006/0010506 A1 | 1/2006 | Otte et al. | |
| 2006/0141577 A1 | 6/2006 | Otte et al. | |
| 2006/0195935 A1 | 8/2006 | Otte et al. | |
| 2007/0128717 A1 | 6/2007 | Otte et al. | |
| 2008/0085537 A1 | 4/2008 | Otte et al. | |

FOREIGN PATENT DOCUMENTS

| | | |
|---|---|---|
| EP | 0724639 B1 | 1/2001 |
| EP | 1 273 666 | 1/2003 |
| WO | WO 91/01374 | 2/1991 |
| WO | WO 96/04390 | 2/1996 |
| WO | WO 96/12008 | 4/1996 |
| WO | WO 97/27207 | 7/1997 |
| WO | WO 98/11207 | 3/1998 |
| WO | WO 98/39411 | 9/1998 |

(Continued)

OTHER PUBLICATIONS

PCT International Search Report, PCT/EP2007/05196, dated Mar. 5, 2008.
PCT International Preliminary Report on Patentability, PCT/EP2004/055794, dated Jan. 26, 2007.
Dummitt et al., N-Terminal Methionine Removal and Methionine Metabolism in *Saccharomyces cervisiae*, Journal of Cellular Biology, 2003, pp. 964-974, vol. 89.
Moser et al., An Update of pTRIDENT Mulicistronic Expression Vectors: pTRIDENTs Containing Novel Streptogramin-Responsive Promoters, Biotechnol. Prog., 2000, pp. 724-735, vol. 16.
Carroll et al., Translation of Equine infectious Anemia Virus Bicistronic tat-rev mRNA Requires Leaky Ribosome Scanning of the tat CTG Codon, Journal of Virology, Mar. 1993, pp. 1433-1440, vol. 67, No. 3.

(Continued)

*Primary Examiner* — Kevin K. Hill
(74) *Attorney, Agent, or Firm* — TraskBritt, P.C.

(57) ABSTRACT

The invention provides a DNA molecule comprising an open reading frame sequence that encodes a selectable marker polypeptide, wherein said DNA molecule in the coding strand comprises a translation start sequence for the selectable marker polypeptide having a GTG startcodon or a TTG startcodon, and wherein the open reading frame sequence that encodes the selectable marker protein has been mutated to replace at least half of its CpG dinucleotides as compared to the native open reading frame sequence that encodes the selectable marker protein.

10 Claims, 3 Drawing Sheets

FOREIGN PATENT DOCUMENTS

Figure 1:
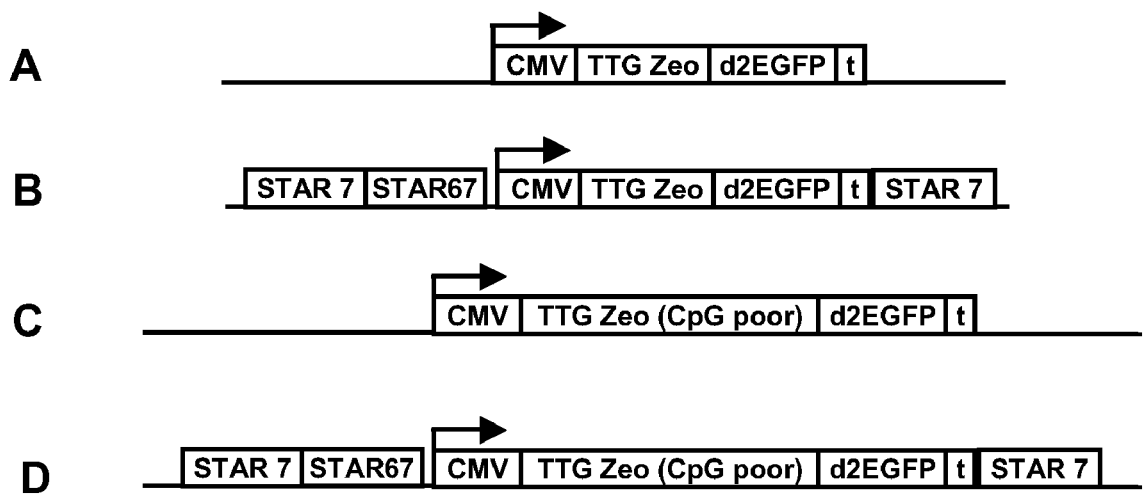
Figure 1:
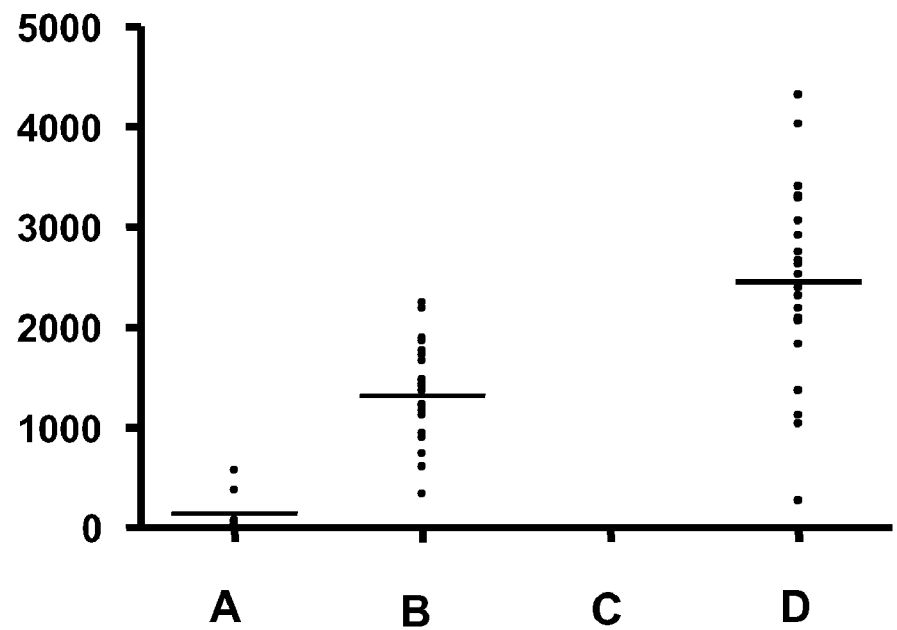

| WO | WO 98/49289 | | 11/1998 |
|---|---|---|---|
| WO | WO 00/05393 | | 2/2000 |
| WO | WO 00/09749 | | 2/2000 |
| WO | WO 00/17337 | | 3/2000 |
| WO | WO 00/23606 | | 4/2000 |
| WO | WO 01/02553 | | 1/2001 |
| WO | WO 01/32901 | | 5/2001 |
| WO | WO 01/57188 | A2 | 8/2001 |
| WO | WO 01/59117 | | 8/2001 |
| WO | WO 01/59118 | | 8/2001 |
| WO | WO 02/24930 | A2 | 3/2002 |
| WO | WO 02/072846 | * | 9/2002 |
| WO | WO 02/074969 | | 9/2002 |
| WO | WO 02/099070 | | 12/2002 |
| WO | WO 02/099089 | | 12/2002 |
| WO | WO 03/004704 | | 1/2003 |
| WO | WO 03/083077 | | 10/2003 |
| WO | WO 03/106684 | | 12/2003 |
| WO | WO 03106684 | | 12/2003 |
| WO | WO 2004/027072 | | 4/2004 |
| WO | WO 2004/055215 | A1 | 7/2004 |
| WO | WO 2004/056986 | A2 | 7/2004 |
| WO | WO 94/23046 | | 10/2004 |
| WO | WO 2005/040377 | | 5/2005 |
| WO | WO 2006/005718 | | 1/2006 |
| WO | WO 2006/048459 | | 5/2006 |
| WO | WO 2006/048459 | A | 5/2006 |
| WO | WO 2007/096399 | | 8/2007 |
| WO | WO 2007/108675 | | 9/2007 |

OTHER PUBLICATIONS

PCT International Search Report, PCT/EP2007/051696, dated Mar. 5, 2008.
PCT Written Opinion, PCT/EP2007/051696 dated Mar. 5, 2008.
PCT International Preliminary Report of Patentability, PCT/EP2007/053984, dated Jul. 25, 2008.
Kozak, M., An analysis of 5'-noncoding sequences from 699 vertebrate messenger RNAs, Nucleic Acids Res., 1987, pp. 8125-48, vol. 15, No. 20.
Kozak, M., Context Effects and Inefficient Initiation at Non-AUG Codons in Eucaryotic Cell-Free Translation Systems, Molecular and Cellular Biology, Nov. 1989, pp. 5073-5080, vol. 9, No. 11.
Kozak, M., Recognition of AUG and alternative initiator codons in augmented by G in position +4 but is not generally affected by the nucleotides in positions +5 and +6. The EMBO Journal, 1997, pp. 2482-2492, vol. 16, No. 9.
Kozak, M., Point Mutations Define a Sequence Flanking the AUG Initiator Codon That Modulates Translation by Eukaryotic Ribosomes, Cell, Jan. 31, 1986, pp. 283-292. vol. 44.
Lee et al., Engineering Chinese hamster ovary (CHO) cells to achieve an inverse growth—associated production of a foreign protein, β-galactosidase, Cytotechnology, 1998, pp. 73-80, vol. 28.
Aranda et al., Definition of Transcriptional Pause Elements in Fission Yeast, Molecular and Cellular Biology, Feb. 1999, pp. 1251-1261, vol. 19, No. 2.
Auten et al., "Effect of Scaffold Attachment Region on Transgene Expression in Retrovirus Vector-Transduced Primary T cells and Macrophages," Human Gene Therapy, May 20, 1999, pp. 1389-1399, vol. 10, No. 8.
Bell et al., Insulators and Boundaries: Versatile Regulatory Elements in the Eukaryotic Genome, Science, pp. 447-450, vol. 291, No. 5503, 2001.
Burgess-Beusse et al., The insulation of genes from external enhancers and silencing chromatin, PNAS, Dec. 10, 2002, pp. 16433-16437, vol. 99, Suppl. 4.
Chan et al., p300-CBP proteins: HATs for transcriptional bridges and scaffolds, Journal of Cell Science, 2001, pp. 2363-2373, vol. 114.
Chung et al., A 5' Element of the Chicken Beta-Globin Domain Serves as an Insulator in Human Erythroid Cells and Protects against Position Effect in Drosophila, Aug. 13, 1993, Cell, pp. 505-514, vol. 74.
Database EMBL 'Online! Dec. 15, 1999, "Homo sapiens BAC clone RP11-572N21 from 2, complete sequence," XP002359988 retrieved from EBI accession No. EM_PRO:AC018470, database accession No. AC018470, for SEQ ID No. 17.
Database EMBL 'Online! Mar. 15, 1999, "Homo sapiens chromosome UNK clone CTA-435J10, working draft sequence, I unordered pieces," XP002359997 retrieved from EBI accession No. EM_PRO:AC007044, database accession No. AC007044 for SEQ ID No. 61.
Database EMBL 'Online! Mar. 19, 1998, CIT-HSP-2172C8.TF CIT-HSP Homo sapiens genomic clone 2172C8, genomic survey sequence, XP002359995 retrieved from EBI accession No. EM_PRO:B92131, database accession No. B92131 for SEQ ID No. 44.
Database EMBL 'Online! Dec. 23, 1999, "Human DNA sequence from clone RP11-54H19 on chromosome 1 Contains the 3' end of the LMNA gene for lamin A/C, the gene for a novel protein similar to semaphorins (FLJ12287), a novel gene (KIAA0446), the PMFI gene for polyamine-modulated factor 1, the BGLAP gene for bone gamma-carboxyglutamate (gla) p," XP002359989, retrived from EBI accession No. EM_PRO:AL135927, database accession No. AL135927 for SEQ ID No. 27.
Database EMBL 'Online! Sep. 24, 2000, "Homo sapiens chromosome 4 clone RP11-680118, working draft sequence, 25 unordered pieces," XP002359987 retrieved from EBI accession No. EM_PRO:AC080087, database accession No. AC080087 for SEQ ID No. 9.
Database EMBL 'Online! Jan. 25, 2001, "QV2-NN0045-081200-535-c10 NN0045 Homo sapiens cDNA, mRNA sequence." XP002359993 retrieved from EBI accession No. EM_PRO:BF960930, database accession No. BF960930 for SEQ ID No. 43.
Database EMBL 'Online! Apr. 26, 2001, "RST28606 Athersys RAGE Library Homo sapiens cDNA, mRNA sequence," XP002359990 retrieved from EBI accession No. EM_PRO:BG209092, database accession No. BG209092 for SEQ ID No. 40.
Database EMBL 'Online! Oct. 28, 1998, "Homo sapiens neurexin III-alpha gene, partial cds," XP002359992, retrieved from EBI accession No. EM_PRO:AF099810, database accession No. AF099810 for SEQ ID No. 43.
Database EMBL ' Online! Sep. 29, 1999, "Homo sapiens genomic DNA, chromosome 22g11.2, Cat Eye Syndrome region, clone:N64E9," XP002359991, retrieved from EBI accession No. EM_PRO: AP000526, database accession No. AP000526 for SEQ ID No. 40.
Database EMBL 'Online! Sep. 29, 1999, Homo sapiens genomic DNA, chromosome 22q11.2, Cat Eye Syndrome region, clone:N14H11, XP002359994 retrieved from EBI accession No. EM_PRO:AP000525, database accession No. AP000525 for SEQ ID No. 44.
Database EMBL 'Online! Sep. 29, 1999, "Homo sapiens genomic DNA, chromosome 22q11.2, Cat Eye Syndrome region, clone:c91G6," XP002359996 retrieved from EBI accession No. EM_PRO:AP000528, database accession No. AP000528 for SEQ ID No. 45.
Database EMBL ' Online! Feb. 3, 2004, "Sequence 33099 from Patent WO02068579," XP002359986 retrieved from EBI accession No. EM_PRO:CQ747165, database accession No. CQ747165 for SEQ ID No. 9.
Database EMBL ' Online! Aug. 4, 1999, "Homo sapiens chromosome 19 clone CTD-2540B15, complete sequence," XP002359985 retrieved from EBI accession No. EM_PRO:AC008738, database accession No. AC008738 for SEQ ID No. 7.
Database EMBL 'Online!, Jul. 8, 1992, H. sapiens HOX4B gene upstream sequence XP002348163 retrieved from EBI, Database accession No. X67079, Abstract.
De Boer et al., Portable Shine-Dalgarno regions; nucleotides between the Shine-Dalgarno sequence and the start codon affect the translation efficiency, Gene Amplification and Analysis, 1983, pp. 103-116, vol. 3.
Eggermont et al., Poly(A) signals and transcriptional pause sites combine to prevent interference between RNA polymerase II promoters, The EEMBO Journal, 1993, pp. 2539-2548, vol. 12, No. 6.

Emery et al., A chromatin insulator protects retrovirus vectors from chromosomal position effects, Proceedings of the National Academy of Sciences of USA, Aug. 1, 2000, pp. 9150-9155, vol. 97, No. 16.
European Search Report dated Dec. 22, 2005.
European Search Report for EP 04 10 5593 dated Jun. 21, 2005.
Farrell et al., Conserved CTCF Insulator Elements Flank the Mouse and Human Beta-Globin Loci, Molecular and Cellular Biology, Jun. 2002, pp. 3820-31, vol. 22. No. 11.
Glucksmann et al., Database accession No. AAH76193, Oct. 29, 2001.
Han et al., "Matrix attachment regions (MARs) enhance transformation frequency and transgene expression in poplar," Transgenic Research, 1997, pp. 415-420, vol. 6.
Hellen et al., Internal ribosome entry sites in eukaryotic mRNA molecules, Genes and Development, 2001, pp. 1593-1612, vol. 15, No. 13, Cold Spring Harbor Laboratory Press.
Johnson et al., Requirements for utilization of CREB binding protein by hypersensitive site two of the Beta-globin locus control region, Nucleic Acids Research 2002, pp. 1522-1530, vol. 30, No. 7.
Kellum et al., A Group of scs Elements Function as Domain Boundaries in an Enhancer-Blocking Assay, Molecular and Cellular Biology, May 1992, pp. 2424-2431, vol. 12, No. 5.
Kozak, Initiation of translation in prokaryotes and eukaryotes, Gene, 1999, pp, 187-208, vol. 234.
Kozak, Pushing the limits of the scanning mechanism for initiation of translation, Gene, 2002, pp. 1-34, vol. 299.
Kuhn et al., Functional Analysis of the Internal Translation Initiation Site of Foot-and-Mouth Disease Virus, Journal of Virology, Oct. 1990, pp. 4625-4631, vol. 64, No. 10.
Kwaks et al., Indentification of anti-repressor elements that confer high stable protein in production in mammalian cells, Nature Biotechnology, May 20, 2003, pp. 553-558, vol. 21, No. 5.
Lopez De Quinto et al., Parameters influencing translational efficiency in aphthovirus IRES-based bicistronic expression vectors, Gene, 1998, pp. 51-56, vol. 217.
Maniatis et al., Recognition Sequences of Repressor and Polymerase in the Operators of Bacteriophage Lambda, Cell, Jun. 1975, pp. 109-113, vol. 5.
Martinez-Balbas et al., The acetyltransferase activity of CBP stimulates transcription, The EMBO Journal, 1998, pp. 2886-2893, vol. 17, No. 10.
Mielke et al., "Stabilized, long-term expression of heterodimeric proteins from tricistronic mRNA," Gene, Aug. 22, 2000, pp. 1-8, vol. 254, No. 1-2.
Migliaccio et al., "Stable and unstable transgene integration sites in the human genome: extinction of the Green Fluorescent Protein transgene in K562 cells," Gene, Oct. 3, 2000, pp. 197-214, vol. 256, No. 1-2.
Partial European Search Report, EP 05 07 6209, dated Oct. 7, 2005.
Pile et al., GAGA Factor-dependent Transcription and Establishment of DNase Hypersensitivity Are Independent and Unrelated Events In Vivo, J. of Biological Chemistry, Jan. 14, 2000, pp. 1398-1404, vol. 275, No. 2.
Reik et al., Biotechnologies and therapeutics: Chromatin as a target, Current Opinion in Genetics & Development, 2002, pp. 233-242, vol. 12.
Seum et al., A GAL4-HP1 fusion protein targeted near heterochromatin promotes gene silencing, Chromosoma, 2000, pp. 453-459, vol. 109.
Sigrist et al., Chromatin Insulator Elements Black the Silencing of a Target Gene by the Drosophila Polycomb Response Element (PRE) but Allow trans Interactions Between PREs on Different Chromosomes, Genetics, Sep. 1997; pp. 209-211, vol. 147, No. 1.
Van Der Vlag et al., Transcription Repression Mediated by Polycomb Group Proteins and Other Chromatin-associated Repressors Is Selectively Blocked by Insulators, Journal of Biological Chemistry, Jan. 7, 2000, pp. 697-704, vol. 275, No. 1.
West et al., Insulators: many functions, many mechanisms, Genes and Development, Feb. 1, 2002, pp. 271-288, vol. 16, No. 3.
PCT International Search Report dated Apr. 24, 2007, International Application No. PCT/EP2007/053984.
Rhazin, CpG methylation, chromatin structure and gene silencing—a three-way connection, The EMBO Journal, 1998, pp. 4905-4908, vol. 17, No. 17.
Bird et al., Methylation-Induced Repression—Belts, Braces and Chromatin, Cell, Nov. 24, 1999, pp. 451-454, vol. 99.
Williams et al., CpG-island fragments from the HNRPA2BI/CBX3 genomics locus reduce silencing and enhance transgene expression from the hCMV promotor/enhancer in mammalian cells, published Jun. 3, 2005, <http://www.biomedcentral.com/1472-6750/5/17>.
Van Blokland et al., A novel, high stringency selection system allos screening of few clones for high protein expression, Journal of Biotechnology, Sep. 22, 2006, pp. 237-245, vol. 128.
Kwaks et al., Targeting of histone acetyltranscerase domain to a promoter enhances protein expression levels in mammalian cells, Journal of Biotechnology, 2005, pp. 35-46, vol. 115.
Kwaks et al., Employing epigenetics to augment the expression of therapeutic proteins in mammalian cells, Trends in Biotechnology, Mar. 2006, pp. 137-142, vol. 24, No. 3.
Otte et al., Various Expression-Augmenting DNA Elements Benefit from STAR-Select, a Novel High Stringency Selection System from Protein Expression, Biotechnol. Pros., 2007, pp. 801-807, vol. 23.
PCT International Search Report, PCT/EP2007/051696, dated Mar. 5, 2008.
Genbank Accesion AY237385.1 (AA089266, GI:37933202); Spyrou, et al.; Molecular analysis of the proviral DNA of eqine infectious anemia virus in mules in Greece; taken from http://www.ncbi.nlm.nih.gov/entrez/viewer.fcgi?db=protein&id=37933202— Accessed on Jul. 23, 2008.
Hennecke et al., Composition and arrangement of genes define the strength of IRES-driven translation in bicistronic mRNAs, Nucleic Acids Res., 2001, pp. 3327-3334, vol. 29, No. 16, Oxford University Press.
Kozak, Downstream secondary structure facilitates recognition of initiator codons by eukaryotic ribosomes, PNAS, 1990, pp. 8301-8305, vol. 87, No. 21.
Ress et al., Bicistronic Vector for the Creation of Stable Mammalian Cell Lines that Predisposes All Antibiotic-Resistant Cells to Express Recombinant Protein, Biotechniques, 1996, pp. 102-110, vol. 20, No. 1, Middlesex, UK.
Tang et al., A transformation system for the nonuniversal CUG[Ser] codon usage species Candida rugosa, J. Microbiol. Methods, 2003, pp. 231-238, vol. 52.
Yew et al., CpG-Depleted Plasmid DNA Vectors with Enhanced Safety and Long-Term Gene Expression in Vivo, Molecular Therapy, 2002, pp. 731-38, vol. 5, The American Society of Gene Therapy.

* cited by examiner

SELECTION OF HOST CELLS EXPRESSING PROTEIN AT HIGH LEVELS

CROSS-REFERENCE TO RELATED APPLICATIONS

This application is the national stage of PCT International Patent Application No. PCT/EP2007/053984, filed on Apr. 24, 2007, designating the United States of America, and published, in English, as PCT International Publication No. WO 2007/128685 A1 on Nov. 15, 2007, which PCT application claims priority to U.S. Ser. No. 11/416,490, filed May 2, 2006, and EP 06113354.2, also filed on May 2, 2006. U.S. patent application Ser. No. 11/416,490 is a continuation-in-part of U.S. patent application Ser. No. 11/269,525, filed Nov. 7, 2005, which application claimed priority under 35 U.S.C. Section 119(e) to U.S. Provisional Patent Application Ser. No. 60/626,301, filed Nov. 8, 2004, and to U.S. Provisional Patent Application Ser. No. 60/696,610, filed Jul. 5, 2005. U.S. patent application Ser. No. 11/269,525 also claims the benefit of EP 04105593.0, filed Nov. 8, 2004. U.S. patent application Ser. No. 11/416,490 is further a continuation-in-part of U.S. patent application Ser. No. 11/359,953, filed Feb. 21, 2006, which itself is a continuation-in-part of U.S. patent application Ser. No. 11/269,525, filed Nov. 7, 2005.

BACKGROUND OF THE INVENTION

Field of the Invention

The invention relates to the field of molecular biology and biotechnology. More specifically the present invention relates to means and methods for improving the selection of host cells that express proteins at high levels.

Proteins can be produced in various host cells for a wide range of applications in biology and biotechnology, for instance as biopharmaceuticals. Eukaryotic and particularly mammalian host cells are preferred for this purpose for expression of many proteins, for instance when such proteins have certain posttranslational modifications such as glycosylation. Methods for such production are well established, and generally entail the expression in a host cell of a nucleic acid (also referred to as 'transgene') encoding the protein of interest. In general, the transgene together with a selectable marker gene is introduced into a precursor cell, cells are selected for the expression of the selectable marker gene, and one or more clones that express the protein of interest at high levels are identified, and used for the expression of the protein of interest.

Methods to select recombinant host cells expressing relatively high levels of desired proteins are known (see, e.g. introductions in WO 2006/048459 and US 2006/0141577).

A novel concept for selecting host cells expressing high levels of polypeptides of interest was disclosed in international application PCT/EP2005/055794 (published as WO 2006/048459), which was filed before but published after the priority date of the instant application. An alternative was disclosed in U.S. patent application Ser. No. 11/359,953 (published as US 2006/0141577) and in international application PCT/EP2007/051696, also filed before but published after the priority date of the instant application. Briefly, those applications teach the use of a sequence encoding a selectable marker polypeptide with a non-ATG startcodon, e.g. a GTG or TTG. This resulted in the possibility to select clones with high stringency and was used to obtain clones of host cells with very high expression levels.

The present invention aims at providing further improved means and methods for selection of host cells expressing high levels of proteins of interest.

BRIEF SUMMARY OF THE INVENTION

The disclosures of applications PCT/EP2005/055794 (WO 2006/048459), U.S. Ser. No. 11/359,953 (US 2006/0141577) and PCT/EP2007/051696 are incorporated in their entirety by reference herein. Briefly, those applications teach the use of a sequence encoding a selectable marker polypeptide with a non-ATG startcodon, e.g. a GTG or TTG. This resulted in the possibility to select clones with high stringency and was used to obtain clones of host cells with very high expression levels.

The present invention discloses improved selectable marker genes with a GTG or TTG startcodon. Such improved selectable marker genes can for instance be used in the transcription units and methods of use thereof described in WO 2006/048459 and US 2006/0141577. This leads to further improved (selection of) host cells with high expression levels.

In one aspect, the invention provides a DNA molecule comprising an open reading frame sequence that encodes a selectable marker polypeptide, wherein said DNA molecule in the coding strand comprises a translation start sequence for the selectable marker polypeptide chosen from the group consisting of: a) a GTG startcodon; and b) a TTG startcodon; and wherein the open reading frame sequence that encodes the selectable marker protein has been mutated to replace at least half of its CpG dinucleotides as compared to the native open reading frame sequence that encodes the selectable marker protein.

In preferred embodiments, the selectable marker protein provides resistance against lethal and/or growth-inhibitory effects of a selection agent, such as an antibiotic. In certain embodiments, the selectable marker polypeptide provides resistance against ZEOCIN™ antibiotic or against neomycin.

The invention further provides a DNA molecule according to the invention, wherein the open reading frame sequence that encodes a selectable marker polypeptide is part of a multicistronic transcription unit that further comprises an open reading frame sequence encoding a polypeptide of interest.

The invention further provides an expression cassette comprising such DNA molecules, said expression cassette comprising a promoter upstream of said multicistronic transcription unit and preferably a transcription termination sequence downstream of the multicistronic transcription unit.

The invention further provides host cells comprising a DNA molecule or an expression cassette according to the invention.

The invention further provides a method of expressing a polypeptide of interest, comprising culturing a host cell comprising the expression cassette of the invention, and expressing the polypeptide of interest from the expression cassette.

LEGENDS TO THE FIGURES

FIG. 1. Results with a ZEOCIN™ antibiotic resistance marker with reduced CpG content in CHO-K1 cells. Dots indicate individual data points; lines indicate the average expression levels; vertical axis indicates d2EGFP signal. See Example 1 for details.

Figure 2:
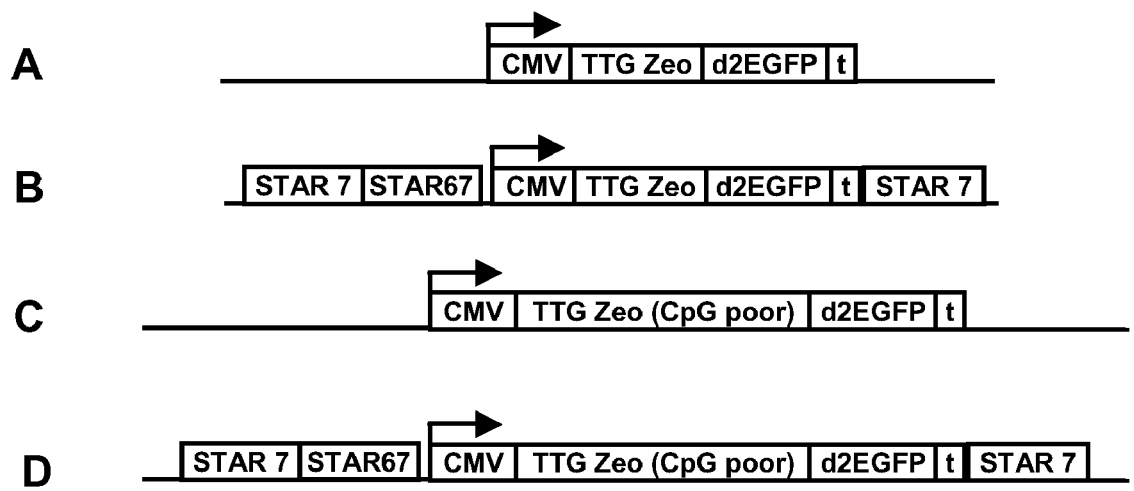
Figure 2:
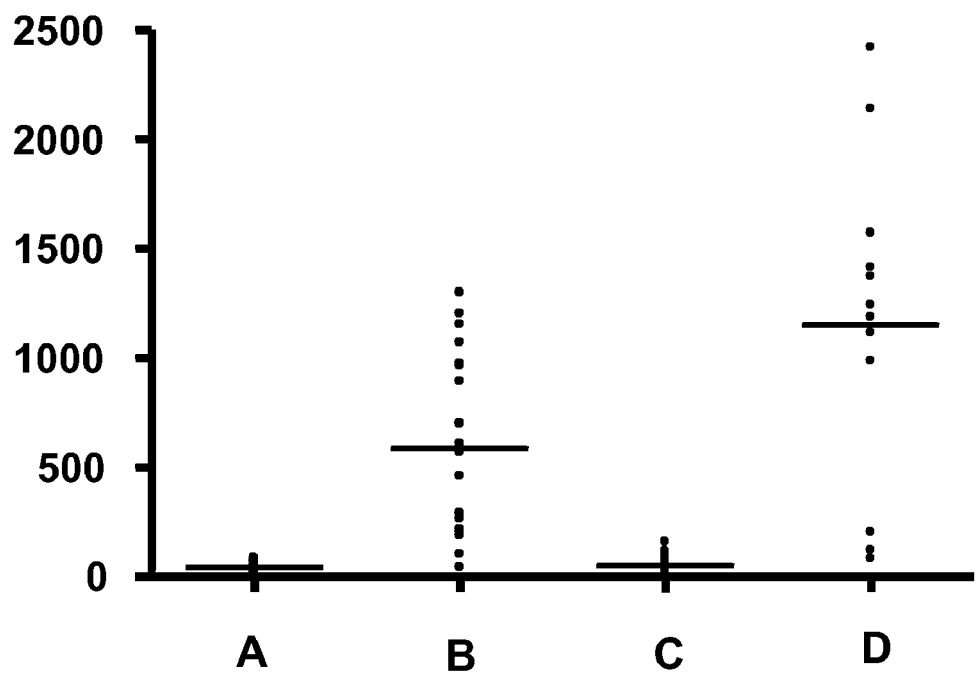

FIG. 2. As FIG. 1, but now in CHO-DG44 cells. See example 1 for details.

Figure 3:
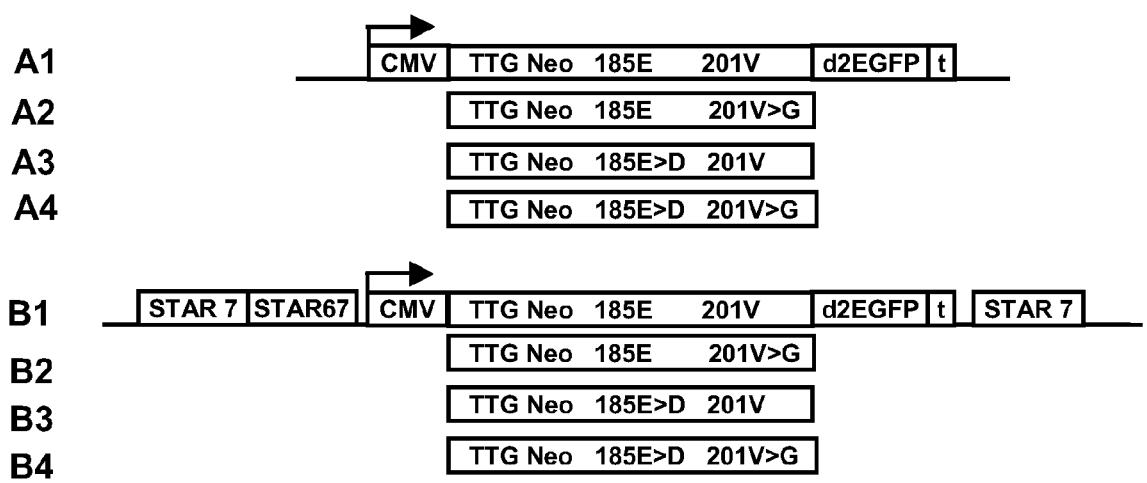
Figure 3:
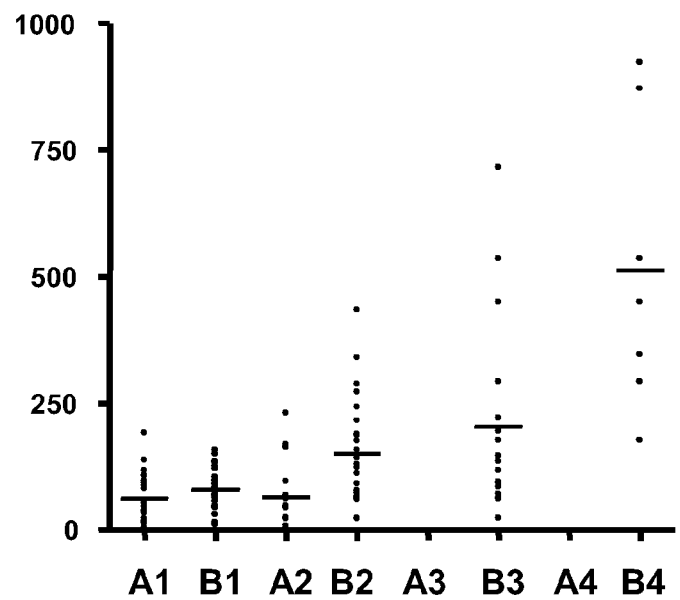

FIG. 3. Results with 'CpG poor' neomycin resistance marker having different mutations. Dots indicate individual data points; lines indicate the average expression levels; vertical axis indicates d2EGFP signal. See example 2 for details.

DETAILED DESCRIPTION OF THE INVENTION

The term "monocistronic gene" is defined as a gene capable of providing a RNA molecule that encodes one polypeptide. A "multicistronic transcription unit", also referred to as multicistronic gene, is defined as a gene capable of providing an RNA molecule that encodes at least two polypeptides. The term "bicistronic gene" is defined as a gene capable of providing a RNA molecule that encodes two polypeptides. A bicistronic gene is therefore encompassed within the definition of a multicistronic gene. A "polypeptide" as used herein comprises at least five amino acids linked by peptide bonds, and can for instance be a protein or a part, such as a subunit, thereof. It may comprise posttranslational modifications, e.g. glycosylation. Mostly, the terms polypeptide and protein are used interchangeably herein. A "gene" or a "transcription unit" as used in the present invention can comprise chromosomal DNA, cDNA, artificial DNA, combinations thereof, and the like. "Operably linked" refers to a situation where the components described are in a relationship permitting them to function in their intended manner. Thus, for example, a promoter "operably linked" to a cistron is ligated in such a manner that expression of the cistron is achieved under conditions compatible with the promoter. Similarly, a nucleotide sequence of an IRES operably linked to a cistron is ligated in such a manner that translation of the cistron is achieved under conditions compatible with the IRES.

The DNA molecules of the invention can be present in the form of double stranded DNA, having with respect to the selectable marker polypeptide and the polypeptide of interest a coding strand and a non-coding strand, the coding strand being the strand with the same sequence as the translated RNA, except for the presence of T instead of U. Hence, an AUG startcodon is coded for in the coding strand by an ATG sequence, and the strand containing this ATG sequence corresponding to the AUG startcodon in the RNA is referred to as the coding strand of the DNA. It will be clear to the skilled person that startcodons or translation initiation sequences are in fact present in an RNA molecule, but that these can be considered equally embodied in a DNA molecule coding for such an RNA molecule; hence, wherever the present invention refers to a startcodon or translation initiation sequence, the corresponding DNA molecule having the same sequence as the RNA sequence but for the presence of a T instead of a U in the coding strand of said DNA molecule is meant to be included, and vice versa, except where explicitly specified otherwise. In other words, a startcodon is for instance an AUG sequence in RNA, but the corresponding ATG sequence in the coding strand of the DNA is referred to as startcodon as well in the present invention. The same is used for the reference of 'in frame' coding sequences, meaning triplets (3 bases) in the RNA molecule that are translated into an amino acid, but also to be interpreted as the corresponding trinucleotide sequences in the coding strand of the DNA molecule.

A translation start sequence is often referred to in the field as 'Kozak sequence', and an optimal Kozak sequence is RCC ATGG, the startcodon underlined, R being a purine, i.e. A or G (see Kozak M, 1986, 1987, 1989, 1990, 1997, 2002). Hence, besides the startcodon itself, the context thereof, in particular nucleotides −3 to −1 and +4, are relevant, and an optimal translation startsequence comprises an optimal startcodon (i.e. ATG) in an optimal context (i.e. the ATG directly preceded by RCC and directly followed by G). Translation by the ribosomes is most efficient when an optimal Kozak sequence is present (see Kozak M, 1986, 1987, 1989, 1990, 1997, 2002). However, in a small percentage of events, non-optimal translation initiation sequences are recognized and used by the ribosome to start translation. The present invention makes use of this principle, and allows for decreasing the amount of translation and hence expression of the selectable marker polypeptide, which can therefore be used to increase the stringency of the selection system.

The term "selection marker" or "selectable marker" is typically used to refer to a gene and/or protein whose presence can be detected directly or indirectly in a cell, for example a polypeptide that inactivates a selection agent and protects the host cell from the agent's lethal or growth-inhibitory effects (e.g. an antibiotic resistance gene and/or protein). Selectable marker polypeptides are well known in the art and routinely used when eukaryotic host cell clones are to be obtained, and several examples of suitable selectable marker proteins are provided in WO 2006/048459. DNA sequences coding for such selectable marker polypeptides are known, and several examples of wild-type sequences of DNA encoding selectable marker proteins are provided in WO 2006/048459 (e.g. FIGS. 15-21 therein, incorporated by reference herein). It will be clear that mutants or derivatives of selectable markers can also be suitably used, and are therefore included within the scope of the term 'selectable marker polypeptide', as long as the selectable marker protein is still functional. For instance any silent mutations that do not alter the encoded protein because of the redundancy of the genetic code are also encompassed. Further mutations that lead to conservative amino acid mutations or to other mutations are also encompassed, as long as the encoded protein still has activity, which may or may not be lower than that of the wild-type protein as encoded by the indicated sequences. In particular, it is preferred that the encoded protein is at least 70%, preferably at least 80%, more preferably at least 90%, still more preferably at least 95% identical to the proteins encoded by the respective indicated sequences. Testing for activity of the selectable marker proteins can be done by routine methods. A selectable marker polypeptide according to the invention is a protein that is encoded by nucleic acid, which polypeptide can be functionally used for selection, for instance because it provides resistance to a selection agent such as an antibiotic. Hence, when an antibiotic is used as a selection agent, the DNA encodes a polypeptide that confers resistance to the selection agent, which polypeptide is the selectable marker polypeptide. The selectable marker polypeptide is encoded by the DNA of the invention. The selectable marker polypeptide according to the invention must be functional in a eukaryotic host cell, and hence being capable of being selected for in eukaryotic host cells. Examples of suitable selectable marker genes for the present invention are zoecin and neomycin. Other suitable candidates include e.g. blasticidin, puromycin, bleomycin, hygromycin, DHFR, GS, etc (see also WO 2006/048459). Other selectable marker genes that could be used, and their selection agents, are for instance described in table 1 of U.S. Pat. No. 5,561,053; see also Kaufman, Methods in Enzymology, 185:537-566 (1990), for a review of these. The term "selection" is typically defined as the process of using a selection marker/selectable marker and a selection agent to identify host cells with specific genetic properties (e.g. that the host cell contains a transgene integrated into its genome). For convenience and as generally accepted by the skilled person, in many publications as well as herein, often the gene and protein encoding the resistance to a selection agent is referred to as the 'selectable agent (resistance) gene' or 'selection agent (resistance) protein', respectively, although the official names may be different, e.g. the gene coding for the protein conferring restance to neomycin (as well as to G418 and kanamycin) is often referred to as neomycin (resistance) (or neo$^r$) gene, while the official name is aminoglycoside 3'-phosphotransferase gene.

The coding sequences of the selectable marker protein of WO 2006/048459 and US 2006/0141577 in preferred embodiments have a GTG or more preferably a TTG startcodon. This results in very stringent selection and very high expression of the protein of interest in the clones that are obtained. In the present invention, the coding sequences of the selectable marker protein are further improved by reducing the CpG content therein, resulting in even higher stringency and further improved expression levels.

Preferably, the translation start sequence in the coding strand for the selectable marker polypeptide comprises a TTG startcodon. Preferably, the GTG or TTG startcodon is flanked by sequences providing for relatively good recognition of the non-ATG sequences as startcodons, such that at least some ribosomes start translation from these startcodons, i.e. the translation start sequence preferably comprises the sequence ACC[GTG or TTG startcodon]G or GCC[GTG or TTG startcodon]G.

In one aspect, the invention provides a DNA molecule comprising an open reading frame sequence that encodes a selectable marker polypeptide, wherein said DNA molecule in the coding strand comprises a translation start sequence for the selectable marker polypeptide chosen from the group consisting of: a) a GTG startcodon; and b) a TTG startcodon; and wherein the open reading frame sequence that encodes the selectable marker protein has been mutated to replace at least 10% of its CpG dinucleotides (any 'CG' in the sequence) as compared to the native open reading frame sequence that encodes the selectable marker protein. Such a DNA molecule can be used according to the invention for obtaining eukaryotic host cells expressing high levels of the polypeptide of interest, by selecting for the expression of the selectable marker polypeptide. Subsequently or simultaneously, one or more host cell(s) expressing the polypeptide of interest can be identified, and further used for expression of high levels of the polypeptide of interest.

It is shown herein that the reduction of the CpG content of the selectable marker gene of the invention, i.e., having a TTG or GTG start codon, can lead to improved expression of a polypeptide of interest that is translated from a multicistronic transcription unit from which also the selectable marker polypeptide is translated. Without wishing to be bound by theory, it is believed that reduction of the CpG content may reduce the possibility for silencing of transcription, because CpG dinucleotides can be methylated and silenced in eukaryotes. Selectable marker polypeptides that are encoded by genes with a relatively high CpG content, often derived from bacterial sequences, for instance ZEOCIN™ antibiotic and neomycin, may benefit most from the reduction of the CpG content, although some benefit may already be found for selection genes with a relatively low CpG content. In certain embodiments, CpG dinucleotides are removed from a sequence encoding a selectable marker polypeptide without changing the encoded amino acid sequence. This can be done by taking advantage of the redundancy of the genetic code, as is well known and routine to the person skilled in the art of molecular biology.

It is expected that a positive effect of removing CpG dinucleotides will be apparent when at least 10% of the CpG dinucleotides in the coding sequence of the selectable marker gene have been replaced. It is expected that removal of more CpG dinucleotides will increase the effect, and hence in certain embodiments, at least 20%, at least 30%, at least 40%, at least 50%, at least 60%, at least 70% or at least 80% of the CpG dinucleotides are mutated compared to the native open reading frame sequence that encodes the selectable marker protein. In certain advantageous embodiments, at least half of the CpG dinucleotides of the open reading frame sequence that encodes the selectable marker polypeptide have been replaced as compared to the native open reading frame sequence that encodes the selectable marker polypeptide.

A native open reading frame sequence that encodes the selectable marker polypeptide that provides resistance to ZEOCIN™ antibiotic is given as SEQ ID NO:1 (containing internal ATGs), and mutation of A at position 280 into T in this sequence gives a sequence lacking internal ATGs, and wherein the internally encoded methionine at position 94 is replaced by leucine. For the DNA sequences of the invention, the start codon (first three nucleotides of the DNA sequences) is mutated into a GTG or into a TTG start codon.

In certain advantageous embodiments, the selectable marker polypeptide provides resistance against ZEOCIN™ antibiotic. In certain embodiments thereof, the DNA molecule comprises SEQ, ID. NO. 1, wherein at least half of the CpG dinucleotides has been replaced without mutating the amino acid sequence that is encoded, with the proviso that the start codon (first three nucleotides in the sequence) is replaced by a start codon chosen from GTG or TTG. In an alternative embodiment, the DNA molecule comprises SEQ ID NO: 1 wherein nucleotide A at position 280 is replaced by T, such that encoded amino acid 94 (methionine) is replaced by leucine, and wherein at least half of the CpG dinucleotides has been replaced without further mutating the amino acid sequence that is encoded, with the proviso that the start codon (first three nucleotides in the sequence) is replaced by a start codon chosen from GTG or TTG. This embodiment lacks ATG sequences in the coding sequence for the ZEOCIN™ antibiotic resistance gene, and is therefore suitable in the multicistronic transcription units of the invention wherein the coding sequence for the selectable marker polypeptide is upstream of the coding sequence for the polypeptide of interest. In one preferred embodiment hereof, the DNA molecule comprises SEQ ID NO: 3.

A native open reading frame sequence that encodes the selectable marker polypeptide that provides resistance to neomycin is given as SEQ. ID. NO. 5 (containing internal ATGs) and as SEQ. ID. NO. 7 (lacking internal ATGs). In advantageous embodiments, these sequences may contain one or more further mutations so that the encoded polypeptide has a mutation of valine at position 201 to glycine (201V>G), of glutamic acid at position 185 to aspartic acid (185E>D), or both (185E>D, 201V>G).

In other advantageous embodiments, the selectable marker polypeptide provides resistance against neomycin. In certain embodiments thereof, the DNA molecule comprises a sequence chosen from the group consisting of any one of: a) SEQ. ID. NO. 5, with the proviso that at least half of the CpG dinucleotides has been replaced without mutating the amino acid sequence that is encoded, and with the further proviso that the startcodon (the first ATG sequence) is replaced by either GTG or TTG; b) SEQ. ID. NO. 7, with the proviso that at least half of the CpG dinucleotides has been replaced without mutating the amino acid sequence that is encoded, and with the further proviso that the startcodon (the first ATG sequence) is replaced by either GTG or TTG; and c) SEQ. ID. NO. 5 or SEQ. ID. NO. 7, containing a mutation to encode a neomycin resistance protein variant as compared to the sequences encoded by the indicated sequences, said variant having glycine at position 201 in the encoded protein (201G variant), or aspartic acid at position 185 (185D variant), or both glycine at position 201 and aspartic acid at position 185 (185D, 201G variant), with the proviso that at least half of the CpG dinucleotides in the given DNA sequence has been replaced without further mutating the amino acid sequence that is encoded, and with the further proviso that the startcodon (the first ATG sequence) is replaced by either GTG or TTG. The 185D variant is for instance obtained by replacing the codon from position 553-555 in the provided nucleic acid sequences with the sequence GAC, and the 201G variant is for instance obtained by replacing the codon from position 601-603 in the provided nucleic acid sequence with GGT. In one preferred embodiment, the DNA molecule comprises SEQ. ID. NO. 9, with the proviso that nucleotide A at position 555 is replaced by C (to encode the 185E>D variant), and that nucleotide T at position 602 is replaced by G and that nucleotide G at position 603 is replaced by T (to encode the 201V>G variant), and with the further proviso that the startcodon (ATG at positions 1-3) is replaced by either GTG or TTG. It will be clear to the skilled person that further variations can be prepared by the skilled person without departing from the teaching of the present invention, and such further variations are encompassed with the present invention as long as the startcodon is not ATG and the encoded protein provides resistance against neomycin (or G418). The 185D and 201G variants further improve the selection stringency according to the present invention.

In certain embodiments, the selectable marker polypeptide further comprises a mutation that reduces the activity of the selectable marker polypeptide compared to its wild-type counterpart. This may be used to increase the stringency of selection even further. As non-limiting examples, proline at position 9 in the ZEOCIN™ antibiotic resistance polypeptide may be mutated, e.g., to Thr or Phe, and for the neomycin resistance polypeptide, amino acid residue 182 or 261 or both may further be mutated (see e.g. WO 01/32901).

In principle, the DNA molecules of the invention, encoding the selectable marker polypeptide, may be used in any expression vector, e.g. as a monocistronic gene. They provide stringent selection criteria. In preferred embodiments however, the ORF that encodes a selectable marker polypeptide is part of a multicistronic transcription unit that further comprises an ORF sequence encoding a polypeptide of interest.

A multicistronic transcription unit according to the invention can for instance be a multicistronic transcription unit comprising sequences coding from 5' to 3' for a selectable marker polypeptide and for a polypeptide of interest, or for instance a multicistronic transcription unit comprising sequences coding from 5' to 3' for a polypeptide of interest and for a selectable marker polypeptide. In the former case, the coding sequence for the selectable marker polypeptide is preferably devoid of ATG sequences in the coding strand (see WO 2006/048459). In the latter case, the polypeptide of interest is encoded upstream from the coding sequence for the selectable marker polypeptide and an internal ribosome entry site (IRES) is operably linked to the sequence encoding the selectable marker polypeptide, and hence the selectable marker polypeptide is dependent from the IRES for its translation (see US 2006/0141577). In one embodiment therefore, a multicistronic transcription unit of the invention comprises in the following order: a) a promoter; b) the sequence encoding the selectable marker protein; and c) a sequence encoding a protein of interest. In another embodiment, a multicistronic transcription unit of the invention comprises in the following order: a) a promoter; b) a sequence encoding a protein of interest; and c) an internal ribosome entry site (IRES), operably linked to d) the sequence encoding the selectable marker protein.

In certain embodiments, the multicistronic transcription units comprise a third cistron downstream of the second cistron, said third cistron preferably operably linked to an IRES, and for instance encoding a second selectable marker polypeptide. This second selectable marker polypeptide in certain embodiments is DHFR, preferably with a GTG or TTG startcodon to allow for continuous selection in dhfr-deficient cells (see, e.g. PCT/EP2007/051696, incorporated by reference herein).

In certain embodiments, the invention provides an expression cassette comprising a DNA molecule of the invention, said expression cassette comprising a promoter upstream of a multicistronic transcription unit of the invention and a transcription termination sequence downstream thereof. Said expression cassette is functional in a eukaryotic host cell for driving transcription of the multicistronic transcription unit.

An 'expression cassette' as used herein is a nucleic acid sequence comprising at least a promoter functionally linked to a sequence of which expression is desired. Preferably, an expression cassette further contains transcription termination and polyadenylation sequences. Examples of suitable promoters and transcription termination/polyadenylation sequences are well known and readily available to the skilled person, and are for instance discussed in WO 2006/048459, p. 28-29, incorporated herein by reference.

Other regulatory sequences such as enhancers may also be included. The promoter must be capable of functioning in a eukaryotic host cell, i.e. it must be capable of driving transcription of the transcription unit. The promoter is thus operably linked to the transcription unit. The expression cassette may optionally further contain other elements known in the art, e.g. splice sites, to comprise introns, and the like. In the embodiments where the selectable marker polypeptide is encoded downstream of the polypeptide of interest, an IRES is operably linked to the cistron that contains the selectable marker polypeptide coding sequence. In the embodiments where the selectable marker polypeptide is encoded upstream of the polypeptide of interest, the sequence encoding the selectable marker polypeptide is devoid of ATG sequences in the coding strand.

As used herein, an "internal ribosome entry site" or "IRES" refers to an element that promotes direct internal ribosome entry to the initiation codon, such as normally an ATG, but in this invention preferably GTG or TTG, of a cistron (a protein encoding region), thereby leading to the cap-independent translation of the gene. IRES sequences and use thereof for expression are well known to the person skilled in the art, as taught in US 2006/0141577 and PCT/EP2007/051696, incorporated by reference herein. See also, e.g., Jackson R J, Howell M T, Kaminski A (1990) Trends Biochem Sci 15 (12): 477-83), Jackson R J and Kaminski, A. (1995) RNA 1 (10): 985-1000, Martinez-Salas, 1999, Venkatesan & Dasgupta, 2001, Rees et al, 1996, and Mizuguchi et al., 2000. An example of a suitable IRES sequence is given in example 19 of US 2006/0141577 (SEQ ID NO. 127 therein), incorporated by reference herein.

DNA molecules according to the invention can be generated by standard molecular biology methods available to the skilled person. For instance, native sequences, e.g. from commercially available plasmids, may be mutated by routine methods. Moreover, it is at present also possible to synthesise at will (if required using subcloning steps) DNA sequences that have sufficient length for an ORF of a selectable marker polypeptide, and such synthetic DNA sequences can nowadays be ordered commercially from various companies. Hence, using the teachings of the present invention, the person skilled in the art may design appropriate sequences according to the invention encoding a selectable marker polypeptide (with a GTG or TTG startcodon, and with reduced CpG content, and in certain embodiments having no internal ATGs), have this sequence synthesized, and test the DNA molecule for functionality of the encoded selectable marker by introducing the DNA molecule in eukaryotic host cells and test for expression of functional selectable marker polypeptide. The commercial availability of such sequences also makes feasible to provide without undue burden for selection marker coding sequences lacking internal ATG sequences, where the wild-type coding sequence of the selection marker polypeptide comprises several such internal ATGs (see WO 2006/048459).

In certain embodiments, a DNA molecule according to the invention is part of a vector, e.g. a plasmid. Such vectors can easily be manipulated by methods well known to the person skilled in the art, and can for instance be designed for being capable of replication in prokaryotic and/or eukaryotic cells. In addition, many vectors can directly or in the form of isolated desired fragment therefrom be used for transformation of eukaryotic cells and will integrate in whole or in part into the genome of such cells, resulting in stable host cells comprising the desired nucleic acid in their genome.

The vector used can be any vector that is suitable for cloning DNA and that can be used for transcription of a nucleic acid of interest. When host cells are used it is preferred that the vector is an integrating vector. Alternatively, the vector may be an episomally replicating vector.

It is widely appreciated that chromatin structure and other epigenetic control mechanisms may influence the expression of transgenes in eukaryotic cells (e.g. Whitelaw et al, 2001). The multicistronic expression units according to the invention form part of a selection system with a rather rigorous selection regime. This generally requires high transcription levels in the host cells of choice. To increase the chance of finding clones of host cells that survive the rigorous selection regime, and possibly to increase the stability of expression in obtained clones, it will generally be preferable to increase the predictability of transcription. Therefore, in preferred embodiments, an expression cassette according to the invention further comprises at least one chromatin control element. A 'chromatin control element' as used herein is a collective term for DNA sequences that may somehow have an effect on the chromatin structure and therewith on the expression level and/or stability of expression of transgenes in their vicinity (they function 'in cis', and hence are placed preferably within 5 kb, more preferably within 2 kb, still more preferably within 1 kb from the transgene) within eukaryotic cells. Such a chromatin control element preferably is chosen from the group consisting of an insulator sequence, a ubiquitous chromatin opener element (UCOE), matrix or scaffold attachment regions (MAR/SAR) and anti-repressor (STAR) sequences. Examples of chromatin control elements, as well as methods for obtaining and using them and functionally testing them, are given in WO 2006/048459, pages 32-37, incorporated by reference herein. In certain embodiments, said at least one chromatin control element is an anti-repressor element chosen from the group consisting of any one of SEQ. ID. NO. 1 through SEQ. ID. NO. 66 of WO 2006/048459, and fragments thereof. In certain embodiments thereof, said expression cassette comprises SEQ. ID. NO. 66 of WO 2006/048459, or a fragment thereof, positioned upstream of the promoter that drives transcription of the multicistronic transcription unit. In other embodiments, the multicistronic transcription unit is flanked on both sides by at least one anti-repressor sequence chosen from the group consisting of any one of SEQ. ID. NO. 1 through SEQ. ID. NO. 65 of WO 2006/048459, or fragments thereof. Preferably, the chromatin control element is chosen from the group consisting of STAR67, STAR7, STAR9, STAR17, STAR27, STAR29, STAR43, STAR44, STAR45, STAR47, STAR61, or a functional fragment or derivative of said STAR sequences (see e.g. WO 2006/048459 for the sequences and preferred uses of these STAR elements, incorporated herein by reference).

A polypeptide of interest according to the invention can be any protein, and may be a monomeric protein or a (part of a) multimeric protein. A multimeric protein comprises at least two polypeptide chains. Non-limiting examples of a protein of interest according to the invention are enzymes, hormones, immunoglobulin chains, therapeutic proteins like anti-cancer proteins, blood coagulation proteins such as Factor VIII, multi-functional proteins, such as erythropoietin, diagnostic proteins, or proteins or fragments thereof useful for vaccination purposes, all known to the person skilled in the art.

The polypeptide of interest may be from any source, and in certain embodiments is a mammalian protein, an artificial protein (e.g. a fusion protein or mutated protein), and preferably is a human protein.

DNA molecules comprising multicistronic transcription units and/or expression cassettes according to the invention can be used for improving expression of nucleic acid, preferably in host cells. The terms "cell"/"host cell" and "cell line"/"host cell line" are respectively typically defined as a cell and homogeneous populations thereof that can be maintained in cell culture by methods known in the art, and that have the ability to express heterologous or homologous proteins. The invention further provides host cells comprising a DNA molecule or an expression cassette according to the present invention.

Prokaryotic host cells can be used to propagate and/or perform genetic engineering with the DNA molecules of the invention, especially when present on plasmids capable of replicating in prokaryotic host cells such as bacteria.

A host cell according to the present invention preferably is a eukaryotic cell, more preferably a mammalian cell, such as a rodent (e.g. mouse, hamster) cell or a human cell or fusion between different cells. In certain non-limiting embodiments, said host cell is a U-2 OS osteosarcoma, HEK 293, HuNS-1 myeloma, WERI-Rb-1 retinoblastoma, BHK, COS, Vero, non-secreting mouse myeloma Sp2/0-Ag 14, non-secreting mouse myeloma NS0, NCI-H295R adrenal gland carcinomal or a PER.C6® cell. PER.C6 cells for the purpose of the present invention means cells from an upstream or downstream passage or a descendent of an upstream or downstream passage of cells as deposited under ECACC no. 96022940 (see e.g. U.S. Pat. No. 5,994,128), i.e. having the characteristics of those cells. It has been previously shown that such cells are capable of expression of proteins at high levels (e.g. WO 00/63403, and Jones et al, 2003). In certain preferred embodiments, the host cells are CHO (Chinese hamster ovary) cells, for instance CHO-K1, CHO-S, CHO-DG44, CHO-DUKXB11, and the like. In certain embodiments, said CHO cells have a dhfr⁻ phenotype.

Such eukaryotic host cells can express desired polypeptides, and are often used for that purpose. They can be obtained by introduction of a DNA molecule of the invention, preferably in the form of an expression cassette, into the cells. Preferably, the expression cassette is integrated in the genome of the host cells, which can be in different positions in various host cells, and selection will provide for a clone where the transgene is integrated in a suitable position, leading to a host cell clone with desired properties in terms of expression levels, stability, growth characteristics, and the like. Alternatively the transcription unit may be targeted or randomly selected for integration into a chromosomal region that is transcriptionally active, e.g. behind a promoter present in the genome.

Preferably the host cells are from a stable clone that can be selected and propagated according to standard procedures known to the person skilled in the art. A culture of such a clone is capable of producing polypeptide of interest, if the cells comprise the transcription unit encoding such.

The invention also provides a method of generating a host cell able to express a polypeptide of interest, said method comprising the steps of: a) introducing into a plurality of precursor cells a DNA molecule or an expression cassette according to the invention, b) culturing the plurality of precursor cells under conditions suitable for expression of the selectable marker polypeptide, and c) selecting at least one host cell expressing the selectable marker polypeptide. Selection for expression of the selectable marker polypeptide is done e.g. by applying selection pressure (e.g. culturing in the presence of selection agent) and will ensure expression of the polypeptide of interest in the multicistronic transcription units and expression cassettes of the invention. This novel method provides a very good result in terms of the ratio of obtained clones versus clones with high expression of the desired polypeptide: far fewer colonies are obtained using the same concentration of selection agent than with known selection systems, and a relatively high percentage of the obtained clones produces the polypeptide of interest at high levels.

The invention further provides a method for producing a polypeptide of interest, comprising culturing a host cell comprising an expression cassette according to the invention, to express the nucleic acid encoding the protein of interest in said cell. In preferred embodiments, the protein of interest is harvested from said cell or from the culture medium or from both. In preferred embodiments, said cell is a mammalian cell, for instance a CHO cell.

Introduction of nucleic acid that is to be expressed in a cell, can be done by one of several methods, which as such are known to the person skilled in the art, also dependent on the format of the nucleic acid to be introduced. Said methods include but are not limited to transfection, infection, injection, transformation, and the like.

In certain embodiments, selection agent is present in the culture medium at least part of the time during the culturing, either in sufficient concentrations to select for cells expressing the selectable marker polypeptide or in lower concentrations. In other embodiments, selection agent is no longer present in the culture medium during the production phase when the polypeptide is expressed.

Culturing a cell is done to enable it to metabolize, and/or grow and/or divide and/or produce recombinant proteins of interest. This can be accomplished by methods well known to persons skilled in the art, and includes but is not limited to providing nutrients for the cell. The methods comprise growth adhering to surfaces, growth in suspension, or combinations thereof. Culturing can be done for instance in dishes, roller bottles or in bioreactors, using batch, fed-batch, continuous systems such as perfusion systems, and the like. In order to achieve large scale (continuous) production of recombinant proteins through cell culture it is preferred in the art to have cells capable of growing in suspension, and it is preferred to have cells capable of being cultured in serum-free, or even protein-free, culture medium.

The conditions for growing or multiplying cells (see e.g. Tissue Culture, Academic Press, Kruse and Paterson, editors (1973)) and the conditions for expression of the recombinant product are known to the person skilled in the art. In general, principles, protocols, and practical techniques for maximizing the productivity of mammalian cell cultures can be found in Mammalian Cell Biotechnology: a Practical Approach (M. Butler, ed., IRL Press, 1991).

In a preferred embodiment, the expressed protein is collected (isolated), either from the cells or from the culture medium or from both. It may then be further purified using known methods, e.g. filtration, column chromatography, etc, by methods generally known to the person skilled in the art.

Obviously, the configurations of the expression cassettes may also be used when the ultimate goal is not the production of a polypeptide of interest, but the RNA itself, for instance for producing increased quantities of RNA from an expression cassette, which may be used for purposes of regulating other genes (e.g. RNAi, antisense RNA), gene therapy, in vitro protein production, etc.

The practice of this invention will employ, unless otherwise indicated, conventional techniques of immunology, molecular biology, microbiology, cell biology, and recombinant DNA, which are within the skill of the art. See e.g. Sambrook, Fritsch and Maniatis, Molecular Cloning: A Laboratory Manual, $2^{nd}$ edition, 1989; Current Protocols in Molecular Biology, Ausubel FM, et al, eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988.

The invention is further explained in the following examples. The examples do not limit the invention in any way. They merely serve to clarify the invention.

EXAMPLES

Example 1

Removing CpG Dinucleotides from the Selectable Marker Coding Sequence Improves Expression Using a Selection Method of the Invention Selection methods using different translation initiation codons for the selectable marker, such as GTG or TTG, can result in very stringent selection, and in very high levels of production for the polypeptide of interest (see, WO 2006/048459 and US 2006/0141577, e.g., Examples 1-19 in the latter). In this example, the coding region of the selectable marker polypeptide gene itself was modified by removing CpG dinucleotides. The rationale is that the C nucleotide in the CpG nucleotide may be prone to methylation, which might result in gene silencing of the selectable marker, and thus removing CpG dinucleotides might improve the results. The ZEOCIN™ antibiotic resistance gene with a TTG start codon was taken as the marker, and as many CpG dinucleotides were removed as was possible, without changing the amino acid sequence of the ZEOCIN™ antibiotic resistance protein, and further without introducing ATG sequences in the coding strand, to prevent undesired translation initiation within the coding region of the ZEOCIN™ antibiotic resistance protein (as explained, e.g., in WO 2006/048459). Hence, some CpG's were not removed. The CpG content of the native sequence (here: containing a TTG start codon, and a mutation to remove the internal ATG sequence) is 13.3%, whereas after mutating the CpG's, the CpG content was reduced to 1.8% [referred to as 'TTG Zeo (CpG poor)']. The ZEOCIN™ antibiotic resistance gene with decreased CpG content was cloned upstream of the d2EGFP coding sequence to result in a multicistronic expression construct. Expression levels of d2EGFP were measured.

Constructs were prepared containing STARs 7 and 67 upstream of the CMV promoter, followed by the TTG Zeo (CpG poor) selection marker (synthesized by GeneArt GmbH, Regensburg, Germany; see SEQ ID NO: 3; see SEQ ID NO: 1 for the ZEOCIN™ antibiotic resistance coding sequence with its natural CpG content), the d2EGFP gene and STAR 7 (FIG. 1). The constructs were transfected to CHO-K1 cells. DNA was transfected using Lipofectamine 2000 (Invitrogen) and cells were grown in the presence of 150 µg/ml ZEOCIN™ antibiotic in HAM-F12 medium (Invitrogen)+ 10% FBS (Invitrogen).

Eight colonies emerged after transfection with the control 'CpG-rich' TTG Zeo construct (A in FIG. 1) and none with the 'CpG-poor' TTG Zeo containing construct (C in FIG. 1). In contrast, with both 'CpG-rich' TTG Zeo (B in FIG. 1) and 'CpG-poor' TTG Zeo (D in FIG. 1) selection markers, more than 24 colonies emerged when STARs 7/67-7 was included in the construct. With the 'CpG-rich' TTG ZEOCIN™ antibiotic selection marker (A in FIG. 1), the average d2EGFP expression with the STAR-less control construct was 140, and with the STAR containing construct 1332 (B in FIG. 1). This is an increase due to the presence of the STAR elements. The average d2EGFP expression with the STAR containing construct and the 'CpG-poor' Zeo was 2453 (D in FIG. 1), an almost two-fold increase in comparison with the 'CpG-rich' TTG Zeo (B in FIG. 1). Furthermore, the highest d2EGFP value achieved with the 'CpG-rich' TTG Zeo construct (B) was 2481 and with the 'CpG-poor' TTG Zeo (D) 4308.

We conclude that lowering the CpG content of the ZEOCIN™ antibiotic marker gene raises the stringency of the selection system. This results in higher d2EGFP expression values when STAR elements are included in the construct and no colonies with the control construct.

The same constructs were also transfected to CHO-DG44 cells. This was done with Lipofectamine 2000 (Invitrogen) and selection was performed with 150 µg/ml ZEOCIN™ antibiotic in the culture medium. The culture medium consisted of HAMF12:DMEM=1:1, +10% fetal bovine serum. With the 'CpG-rich' TTG ZEOCIN™ antibiotic selection marker, the average d2EGFP expression with the STAR-less control construct was 43 (A in FIG. 2), and the average d2EGFP expression with the STAR containing constructs was 586 (B in FIG. 2). This is an increase due to the presence of the STAR elements. The average d2EGFP expression with the STAR constructs and the 'CpG-poor' Zeo was 1152 (D in FIG. 2), an almost two-fold increase in comparison with the 'CpG-rich' TTG Zeo (B in FIG. 2). Furthermore, the highest d2EGFP value achieved with the 'CpG-rich' TTG Zeo construct was 1296 (B in FIG. 2) and with the 'CpG-poor' TTG Zeo 2416 (D in FIG. 2). In contrast with CHO-K1, where no control colonies emerged with the 'CpG-poor' TTG Zeo construct (C in FIG. 1), control colonies emerged with CHO-DG44, but the average d2EGFP value was 52 and the highest value in a colony was 115 (C in FIG. 2).

We conclude that also in CHO-DG44 addition of the 'CpG-poor' TTG Zeo selection marker to the construct results in higher protein expression when STAR elements are employed.

Example 2

Modifications in the Neomycin Resistance Coding Sequence in the Selection System of the Invention In this example, besides the startcodon, also the coding region of the neomycin resistance gene was modified, by removing as many CpG dinucleotides of the (ATG-less, so already devoid of ATG sequences in the coding strand) neomycin resistance gene as possible, while not changing the amino acid sequence of the neomycin resistance protein (except for the Met>Leu mutations where the internal ATG sequences were in-frame and replaced by CTG as compared to the wild-type sequence: obviously this was done for reasons of removing ATG sequences from the coding strand and independent from the effort of reducing the CpG content, see example 17 of WO 2006/048459), and without introducing new ATG sequences in the coding strand, analogously to what was done in example 1 for the zeocin resistance gene. The CpG content of the 'wild type' neomycin selection marker gene is 10.4% (SEQ. ID. NO. 5), while after the changes the CpG content was reduced to 2.3% (SEQ. ID. NO. 9). Constructs containing the sequences for the neomycin resistance gene in this example were ordered from GeneArt GmbH, Regensburg, Germany. As a startcodon, TTG was used in this example. The sequences used therefore consisted of SEQ. ID. NO. 9, with the proviso that the startcodon (first three nucleotides, ATG) was replaced by a TTG startcodon, and further in certain cases contained one of the mutations indicated below.

In the 'CpG poor' neomycin resistance gene, some mutations were made to change amino acids in the neomycin resistance protein, to test whether these have influence on the expression levels of the polypeptide of interest when used in the multicistronic transcription units of the invention. The mutations (Sautter et al, 2005; it is noted that the neo sequence used in the present application encodes three additional amino acids immediately after the startcodon as compared to the sequence used by (Sautter et al, 2005), and hence the amino acid numbering in the present application is three higher as compared to the numbering in (Sautter et al, 2005)) consisted of a change from amino acid valine 201 (198 in Sautter et al, 2005) to glycine 201 (TTG Neo 201V>G), glutamic acid 185 (182 in Sautter et al, 2005) to aspartic acid 185 (TTG Neo 185E>D) and a double mutation in which both amino acid valine 201 and glutamic acid 185 were changed to glycine 201 and aspartic acid 185, respectively (TTG Neo 185E>D/201V>G) (FIG. 3). These modifications were compared with the control Neomycin (CpG poor TTG Neo 185E/201V). In all cases constructs were prepared with and without STAR elements (FIG. 3).

The modified TTG Neo selection marker was incorporated in a construct containing STARs 7 and 67 upstream of the CMV promoter, followed by the TTG Neo selection marker, the d2EGFP gene and STAR 7 (FIG. 3). The constructs were transfected to CHO-K1 cells. DNA was transfected using Lipofectamine 2000 (Invitrogen) and cells were grown in the presence of 500 µg/ml G418 geneticin in HAM-F12 medium (Invitrogen)+10% FBS (Invitrogen).

With the control Neo construct (185E/201V) only a very limited effect of STAR elements was observed. This may at least in part be due to the numerous colonies that were generated under 500 µg/ml G418 geneticin, indicating that the stringency of the TTG neomycin modification is low. However, the neomycin with modifications of the invention is operational: in the TTG Neo 185E 201V construct all ATGs were removed from the coding strand of the neomycin resistance gene, and although d2EGFP values were low, it is clear that the removal of ATGs still allowed proper selection under Geneticin selection pressure. When the Neomycin resistance gene was further modified, a distinctive effect of the addition of STAR elements was observed. The mean of 21 TTG Neo 201V>G control colonies was 65 (A2 in FIG. 3), whereas the mean d2EGFP signal of the 24 TTG Neo 201V>G colonies with STAR elements was 150 (B2 in FIG. 3). The selection stringency with the TTG Neo 185E>D mutation was further increased, since no control colonies survived without STAR elements (A3 in FIG. 3), whereas the mean d2EGFP signal of 17 surviving TTG Neo 185E>D STAR colonies was 204 (B3 in FIG. 3). This mean GFP fluorescence is higher than with the TTG Neo 201V>G colonies (B2 in FIG. 3). Also the highest d2EGFP value in TTG Neo 185E>D colonies was 715, as compared to 433 in the TTG Neo 201V>G colonies (compare B3 and B2 in FIG. 3). The highest stringency was observed in the double Neo mutant, TTG Neo 185E>D 201V>G. No control colonies survived (A4 in FIG. 3) and the mean d2EGFP value of 7 surviving STAR TTG Neo 185E>D 201V>G colonies was 513, with as highest d2EGFP value 923 (B4 in FIG. 3).

It is concluded that the introduction of specific mutations raises the stringency of selection of the Neomycin resistance gene when used according to the invention. Some of these modifications convey such selection stringency to the Neomycin resistance gene that only after incorporation with STAR elements colonies are able to survive, due to higher expression values. This concomitantly results in higher d2EGFP expression values. Clearly, the advantageous embodiments described herein of the neomycin resistance gene further improve the suitability of this gene for use according to the present invention.

It will be clear that the configuration where a neomycin resistance gene with decreased CpG content and with a GTG or TTG start codon, and with the indicated mutations (185E>D and/or 201V>G) could also be placed downstream from the coding sequence for the polypeptide of interest (here d2EGFP as a model) when the neomycin resistance protein coding sequences are placed under control of an IRES (see, e.g., Example 19 in US 2006/0141577). The same holds for the ZEOCIN™ antibiotic resistance gene (Example 1). In such case, no care needs to be taken that mutation of CpG dinucleotides would introduce ATG sequences. It is expected that also in such embodiments, good results can be obtained, i.e., that reduction of the CpG content and specific mutation at the indicated positions of the selectable marker protein coding sequence will improve expression levels.

REFERENCES

Jones D, Kroos N, Anema R, Van Montfort B, Vooys A, Van Der Kraats S, Van Der Helm E, Smits S, Schouten J, Brouwer K, Lagerwerf F, Van Berkel P, Opstelten D-J, Logtenberg T, Bout A (2003) High-level expression of recombinant IgG in the human cell line PER.C6. *Biotechnol. Prog.* 19: 163-168.

Kozak M. (1986) Point mutations define a sequence flanking the AUG initiator codon that modulates translation by eukaryotic ribosomes. *Cell* 44: 283-292.

Kozak M. (1987) An analysis of 5'-noncoding sequences from 699 vertebrate messenger RNAs. *Nucleic Acids Res.* 15: 8125-8148.

Kozak M. (1989) Context effects and inefficient initiation at non-AUG codons in eucaryotic cell-free translation systems. *Mol Cell Biol.* 9: 5073-5080.

Kozak M. (1990) Downstream secondary structure facilitates recognition of initiator codons by eukaryotic ribosomes. *Proc Natl Acad Sci USA* 87:8301-8305.

Kozak M. (1997) Recognition of AUG and alternative initiator codons is augmented by G in position +4 but is not generally affected by the nucleotides in positions +5 and +6. *EMBO J.* 16: 2482-2492.

Kozak M. (2002) Pushing the limits of the scanning mechanism for initiation of translation. *Gene* 299: 1-34.

Martinez-Salas, E. (1999) Internal ribosome entry site biology and its use in expression vectors *Curr Opin Biotechnol* 10, 458-64.

Mizuguchi, H, Xu, Z, Ishii-Watabe, A, Uchida, E, and Hayakawa, T. (2000) IRES-dependent second gene expression is significantly lower than cap-dependent first gene expression in a bicistronic vector *Mol Ther* 1, 376-82.

Rees, S, Coote, J, Stables, J, Goodson, S, Harris, S, and Lee, MG. (1996) Bicistronic vector for the creation of stable mammalian cell lines that predisposes all antibiotic-resistant cells to express recombinant protein *Biotechniques* 20, 102-104, 106, 108-110.

Sautter, K, Enenkel, B. 2005. Selection of high-producing CHO cells using NPT selection marker with reduced enzyme activity. *Biotechnol Bioeng.* 89, 530-538.

Venkatesan, A, and Dasgupta, A. (2001) Novel fluorescence-based screen to identify small synthetic internal ribosome entry site elements *Mol Cell Biol* 21, 2826-37.

Whitelaw, E, Sutherland, H, Kearns, M, Morgan, H, Weaving, L, and Garrick, D. (2001) Epigenetic effects on transgene expression *Methods Mol Biol* 158, 351-68.

The invention claimed is:

1. A DNA molecule comprising an open reading frame polynucleotide that encodes a selectable marker polypeptide, wherein the DNA molecule, in the coding strand for the selectable marker polypeptide, has a GTG start codon or a TTG start codon, and wherein the open reading frame polynucleotide that encodes the selectable marker protein has been mutated to replace at least half of its CpG dinucleotides as compared to the native open reading frame polynucleotide that encodes the selectable marker protein, wherein the DNA molecule comprises SEQ ID NO:3.

2. The DNA molecule of claim 1, wherein the open reading frame polynucleotide that encodes a selectable marker polypeptide is part of a multicistronic transcription unit that further comprises an open reading frame polynucleotide encoding a polypeptide of interest.

3. The DNA molecule of claim 2, wherein the open reading frame polynucleotide that encodes the selectable marker polypeptide is upstream of the open reading frame polynucleotide encoding the polypeptide of interest, and wherein the open reading frame polynucleotide that encodes the selectable marker polypeptide has no ATG sequence in the coding strand.

4. The DNA molecule of claim 2, wherein the open reading frame polynucleotide encoding the polypeptide of interest is upstream of the open reading frame polynucleotide that encodes the selectable marker polypeptide, and wherein the open reading frame polynucleotide that encodes the selectable marker polypeptide is operably linked to an internal ribosome entry site.

5. An expression cassette comprising the DNA molecule of claim 2, said expression cassette comprising a promoter upstream of said multicistronic expression unit and a transcription termination sequence downstream of the multicistronic expression unit.

6. The expression cassette of claim 5, further comprising at least one chromatin control element.

7. A host cell comprising the DNA molecule claim 1.

8. A method of generating a host cell able to express a polypeptide of interest, said method comprising the steps of:
   a) introducing into each of a plurality of precursor cells a DNA molecule according to claim 2,
   b) culturing the plurality of precursor cells under conditions suitable for expression of the selectable marker polypeptide, and
   c) selecting at least one host cell expressing the polypeptide of interest.

9. A method of expressing a polypeptide of interest, the method comprising:
   culturing a host cell comprising the expression cassette of claim 5, and
   expressing the polypeptide of interest from the expression cassette.

10. The method according to claim 9, further comprising harvesting the polypeptide of interest.

* * * * *

UNITED STATES PATENT AND TRADEMARK OFFICE
CERTIFICATE OF CORRECTION

PATENT NO. : 8,039,230 B2
APPLICATION NO. : 12/226706
DATED : October 18, 2011
INVENTOR(S) : Arie Pieter Otte et al.

It is certified that error appears in the above-identified patent and that said Letters Patent is hereby corrected as shown below:

On the title page:
In ITEM (75) Inventors:   Change "Amhem" to --Arnhem--
 (last line)

In ITEM (56) References Cited
 OTHER PUBLICATIONS
 Page 2, 2nd column, 2nd line of the
  8th entry (line 41),   Change "22g11.2," to --22q11.2,--

Signed and Sealed this
Nineteenth Day of February, 2013

Teresa Stanek Rea
*Acting Director of the United States Patent and Trademark Office*

SEQUENCE LISTING

```
<160> NUMBER OF SEQ ID NOS: 10

<210> SEQ ID NO 1
<211> LENGTH: 375
<212> TYPE: DNA
<213> ORGANISM: Artificial
<220> FEATURE:
<223> OTHER INFORMATION: wt zeocin resistance gene
<220> FEATURE:
<221> NAME/KEY: CDS
<222> LOCATION: (1)..(375)

<400> SEQUENCE: 1 atg gcc aag ttg acc agt gcc gtt ccg gtg ctc acc gcg cgc gac gtc      48
Met Ala Lys Leu Thr Ser Ala Val Pro Val Leu Thr Ala Arg Asp Val
1               5                   10                  15 gcc gga gcg gtc gag ttc tgg acc gac cgg ctc ggg ttc tcc cgg gac      96
Ala Gly Ala Val Glu Phe Trp Thr Asp Arg Leu Gly Phe Ser Arg Asp
```

```
ttc gtg gag gac gac ttc gcc ggt gtg gtc cgg gac gac gtg acc ctg      144
Phe Val Glu Asp Asp Phe Ala Gly Val Val Arg Asp Asp Val Thr Leu
         35                  40                  45 ttc atc agc gcg gtc cag gac cag gtg gtg ccg gac aac acc ctg gcc      192
Phe Ile Ser Ala Val Gln Asp Gln Val Val Pro Asp Asn Thr Leu Ala
 50                  55                  60 tgg gtg tgg gtg cgc ggc ctg gac gag ctg tac gcc gag tgg tcg gag      240
Trp Val Trp Val Arg Gly Leu Asp Glu Leu Tyr Ala Glu Trp Ser Glu
 65                  70                  75                  80 gtc gtg tcc acg aac ttc cgg gac gcc tcc ggg ccg gcc atg acc gag      288
Val Val Ser Thr Asn Phe Arg Asp Ala Ser Gly Pro Ala Met Thr Glu
                 85                  90                  95 atc ggc gag cag ccg tgg ggg cgg gag ttc gcc ctg cgc gac ccg gcc      336
Ile Gly Glu Gln Pro Trp Gly Arg Glu Phe Ala Leu Arg Asp Pro Ala
             100                 105                 110 ggc aac tgc gtg cac ttc gtg gcc gag gag cag gac tga                  375
Gly Asn Cys Val His Phe Val Ala Glu Glu Gln Asp
         115                 120

<210> SEQ ID NO 2
<211> LENGTH: 124
<212> TYPE: PRT
<213> ORGANISM: Artificial
<220> FEATURE:
<223> OTHER INFORMATION: Synthetic Construct

<400> SEQUENCE: 2

Met Ala Lys Leu Thr Ser Ala Val Pro Val Leu Thr Ala Arg Asp Val
  1               5                  10                  15

Ala Gly Ala Val Glu Phe Trp Thr Asp Arg Leu Gly Phe Ser Arg Asp
             20                  25                  30

Phe Val Glu Asp Asp Phe Ala Gly Val Val Arg Asp Asp Val Thr Leu
         35                  40                  45

Phe Ile Ser Ala Val Gln Asp Gln Val Val Pro Asp Asn Thr Leu Ala
 50                  55                  60

Trp Val Trp Val Arg Gly Leu Asp Glu Leu Tyr Ala Glu Trp Ser Glu
 65                  70                  75                  80

Val Val Ser Thr Asn Phe Arg Asp Ala Ser Gly Pro Ala Met Thr Glu
                 85                  90                  95

Ile Gly Glu Gln Pro Trp Gly Arg Glu Phe Ala Leu Arg Asp Pro Ala
             100                 105                 110

Gly Asn Cys Val His Phe Val Ala Glu Glu Gln Asp
         115                 120

<210> SEQ ID NO 3
<211> LENGTH: 375
<212> TYPE: DNA
<213> ORGANISM: Artificial
<220> FEATURE:
<223> OTHER INFORMATION: CpG poor and ATG-less zeocin (Zeo) resistance
      sequence
<220> FEATURE:
<221> NAME/KEY: CDS
<222> LOCATION: (1)..(375)

<400> SEQUENCE: 3 ttg gcc aag ttg acc agt gct gtc cca gtg ctc aca gcc agg gac gtg       48
Leu Ala Lys Leu Thr Ser Ala Val Pro Val Leu Thr Ala Arg Asp Val
  1               5                  10                  15 gct gga gct gtt gag ttc tgg act gac agg ttg ggg ttc tcc aga gat       96
Ala Gly Ala Val Glu Phe Trp Thr Asp Arg Leu Gly Phe Ser Arg Asp
```

```
ttt gtg gag gac gac ttt gca ggt gtg gtc aga gac gac gtc acc ctg      144
Phe Val Glu Asp Asp Phe Ala Gly Val Val Arg Asp Asp Val Thr Leu
         35                  40                  45 ttc atc tca gca gtc cag gac cag gtg gtg cct gac aac acc ctg gct      192
Phe Ile Ser Ala Val Gln Asp Gln Val Val Pro Asp Asn Thr Leu Ala
 50                  55                  60 tgg gtg tgg gtg aga gga ctg gac gag ctg tac gct gag tgg agt gag      240
Trp Val Trp Val Arg Gly Leu Asp Glu Leu Tyr Ala Glu Trp Ser Glu
 65                  70                  75                  80 gtg gtc tcc acc aac ttc agg gac gcc agt ggc cct gcc ttg aca gag      288
Val Val Ser Thr Asn Phe Arg Asp Ala Ser Gly Pro Ala Leu Thr Glu
                 85                  90                  95 att gga gag cag ccc tgg ggg aga gag ttt gcc ctg aga gac cca gca      336
Ile Gly Glu Gln Pro Trp Gly Arg Glu Phe Ala Leu Arg Asp Pro Ala
            100                 105                 110 ggc aac tgt gtg cac ttt gtg gca gag gag cag gac tga                  375
Gly Asn Cys Val His Phe Val Ala Glu Glu Gln Asp
            115                 120
```

<210> SEQ ID NO 4
<211> LENGTH: 124
<212> TYPE: PRT
<213> ORGANISM: Artificial
<220> FEATURE:
<223> OTHER INFORMATION: Synthetic Construct

<400> SEQUENCE: 4

```
Leu Ala Lys Leu Thr Ser Ala Val Pro Val Leu Thr Ala Arg Asp Val
 1               5                  10                  15

Ala Gly Ala Val Glu Phe Trp Thr Asp Arg Leu Gly Phe Ser Arg Asp
             20                  25                  30

Phe Val Glu Asp Asp Phe Ala Gly Val Val Arg Asp Asp Val Thr Leu
         35                  40                  45

Phe Ile Ser Ala Val Gln Asp Gln Val Val Pro Asp Asn Thr Leu Ala
 50                  55                  60

Trp Val Trp Val Arg Gly Leu Asp Glu Leu Tyr Ala Glu Trp Ser Glu
 65                  70                  75                  80

Val Val Ser Thr Asn Phe Arg Asp Ala Ser Gly Pro Ala Leu Thr Glu
                 85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
            115                 120
```

<210> SEQ ID NO 5
<211> LENGTH: 804
<212> TYPE: DNA
<213> ORGANISM: Artificial
<220> FEATURE:
<223> OTHER INFORMATION: wild type neomycin (Neo) resistance sequence
<220> FEATURE:
<221> NAME/KEY: CDS
<222> LOCATION: (1)..(804)

<400> SEQUENCE: 5

```
atg gga tcg gcc att gaa caa gat gga ttg cac gca ggt tct ccg gcc       48
Met Gly Ser Ala Ile Glu Gln Asp Gly Leu His Ala Gly Ser Pro Ala
 1               5                  10                  15 gct tgg gtg gag agg cta ttc ggc tat gac tgg gca caa cag aca atc       96
Ala Trp Val Glu Arg Leu Phe Gly Tyr Asp Trp Ala Gln Gln Thr Ile
             20                  25                  30
```

```
ggc tgc tct gat gcc gcc gtg ttc cgg ctg tca gcg cag ggg cgc ccg    144
Gly Cys Ser Asp Ala Ala Val Phe Arg Leu Ser Ala Gln Gly Arg Pro
         35                  40                  45 gtt ctt ttt gtc aag acc gac ctg tcc ggt gcc ctg aat gaa ctg cag    192
Val Leu Phe Val Lys Thr Asp Leu Ser Gly Ala Leu Asn Glu Leu Gln
 50                  55                  60 gac gag gca gcg cgg cta tcg tgg ctg gcc acg acg ggc gtt cct tgc    240
Asp Glu Ala Ala Arg Leu Ser Trp Leu Ala Thr Thr Gly Val Pro Cys
 65                  70                  75                  80 gca gct gtg ctc gac gtt gtc act gaa gcg gga agg gac tgg ctg cta    288
Ala Ala Val Leu Asp Val Val Thr Glu Ala Gly Arg Asp Trp Leu Leu
                 85                  90                  95 ttg ggc gaa gtg ccg ggg cag gat ctc ctg tca tct cac ctt gct cct    336
Leu Gly Glu Val Pro Gly Gln Asp Leu Leu Ser Ser His Leu Ala Pro
            100                 105                 110 gcc gag aaa gta tcc atc atg gct gat gca atg cgg cgg ctg cat acg    384
Ala Glu Lys Val Ser Ile Met Ala Asp Ala Met Arg Arg Leu His Thr
        115                 120                 125 ctt gat ccg gct acc tgc cca ttc gac cac caa gcg aaa cat cgc atc    432
Leu Asp Pro Ala Thr Cys Pro Phe Asp His Gln Ala Lys His Arg Ile
130                 135                 140 gag cga gca cgt act cgg atg gaa gcc ggt ctt gtc gat cag gat gat    480
Glu Arg Ala Arg Thr Arg Met Glu Ala Gly Leu Val Asp Gln Asp Asp
145                 150                 155                 160 ctg gac gaa gag cat cag ggg ctc gcg cca gcc gaa ctg ttc gcc agg    528
Leu Asp Glu Glu His Gln Gly Leu Ala Pro Ala Glu Leu Phe Ala Arg
                165                 170                 175 ctc aag gcg cgc atg ccc gac ggc gag gat ctc gtc gtg acc cat ggc    576
Leu Lys Ala Arg Met Pro Asp Gly Glu Asp Leu Val Val Thr His Gly
            180                 185                 190 gat gcc tgc ttg ccg aat atc atg gtg gaa aat ggc cgc ttt tct gga    624
Asp Ala Cys Leu Pro Asn Ile Met Val Glu Asn Gly Arg Phe Ser Gly
        195                 200                 205 ttc atc gac tgt ggc cgg ctg ggt gtg gcg gac cgc tat cag gac ata    672
Phe Ile Asp Cys Gly Arg Leu Gly Val Ala Asp Arg Tyr Gln Asp Ile
210                 215                 220 gcg ttg gct acc cgt gat att gct gaa gag ctt ggc ggc gaa tgg gct    720
Ala Leu Ala Thr Arg Asp Ile Ala Glu Glu Leu Gly Gly Glu Trp Ala
225                 230                 235                 240 gac cgc ttc ctc gtg ctt tac ggt atc gcc gct ccc gat tcg cag cgc    768
Asp Arg Phe Leu Val Leu Tyr Gly Ile Ala Ala Pro Asp Ser Gln Arg
                245                 250                 255 atc gcc ttc tat cgc ctt ctt gac gag ttc ttc tga                    804
Ile Ala Phe Tyr Arg Leu Leu Asp Glu Phe Phe
            260                 265

<210> SEQ ID NO 6
<211> LENGTH: 267
<212> TYPE: PRT
<213> ORGANISM: Artificial
<220> FEATURE:
<223> OTHER INFORMATION: Synthetic Construct

<400> SEQUENCE: 6

Met Gly Ser Ala Ile Glu Gln Asp Gly Leu His Ala Gly Ser Pro Ala
 1               5                  10                  15

Ala Trp Val Glu Arg Leu Phe Gly Tyr Asp Trp Ala Gln Gln Thr Ile
             20                  25                  30

Gly Cys Ser Asp Ala Ala Val Phe Arg Leu Ser Ala Gln Gly Arg Pro
         35                  40                  45
```

```
Val Leu Phe Val Lys Thr Asp Leu Ser Gly Ala Leu Asn Glu Leu Gln
 50                  55                  60

Asp Glu Ala Ala Arg Leu Ser Trp Leu Ala Thr Thr Gly Val Pro Cys
 65                  70                  75                  80

Ala Ala Val Leu Asp Val Val Thr Glu Ala Gly Arg Asp Trp Leu Leu
                 85                  90                  95

Leu Gly Glu Val Pro Gly Gln Asp Leu Leu Ser Ser His Leu Ala Pro
             100                 105                 110

Ala Glu Lys Val Ser Ile Met Ala Asp Ala Met Arg Arg Leu His Thr
         115                 120                 125

Leu Asp Pro Ala Thr Cys Pro Phe Asp His Gln Ala Lys His Arg Ile
     130                 135                 140

Glu Arg Ala Arg Thr Arg Met Glu Ala Gly Leu Val Asp Gln Asp Asp
145                 150                 155                 160

Leu Asp Glu Glu His Gln Gly Leu Ala Pro Ala Glu Leu Phe Ala Arg
                 165                 170                 175

Leu Lys Ala Arg Met Pro Asp Gly Glu Asp Leu Val Val Thr His Gly
             180                 185                 190

Asp Ala Cys Leu Pro Asn Ile Met Val Glu Asn Gly Arg Phe Ser Gly
         195                 200                 205

Phe Ile Asp Cys Gly Arg Leu Gly Val Ala Asp Arg Tyr Gln Asp Ile
     210                 215                 220

Ala Leu Ala Thr Arg Asp Ile Ala Glu Glu Leu Gly Gly Glu Trp Ala
225                 230                 235                 240

Asp Arg Phe Leu Val Leu Tyr Gly Ile Ala Ala Pro Asp Ser Gln Arg
                 245                 250                 255

Ile Ala Phe Tyr Arg Leu Leu Asp Glu Phe Phe
             260                 265
```

<210> SEQ ID NO 7
<211> LENGTH: 804
<212> TYPE: DNA
<213> ORGANISM: Artificial
<220> FEATURE:
<223> OTHER INFORMATION: modified neomycin resistance gene lacking internal ATG sequences
<220> FEATURE:
<221> NAME/KEY: CDS
<222> LOCATION: (1)..(804)

<400> SEQUENCE: 7

```
atg gga tcg gcc att gaa caa gac gga ttg cac gca ggt tct ccg gcc      48
Met Gly Ser Ala Ile Glu Gln Asp Gly Leu His Ala Gly Ser Pro Ala
 1               5                  10                  15 gct tgg gtg gag agg cta ttc ggc tac gac tgg gca caa cag aca atc      96
Ala Trp Val Glu Arg Leu Phe Gly Tyr Asp Trp Ala Gln Gln Thr Ile
             20                  25                  30 ggc tgc tct gac gcc gcc gtg ttc cgg ctg tca gcg cag ggg cgc ccg     144
Gly Cys Ser Asp Ala Ala Val Phe Arg Leu Ser Ala Gln Gly Arg Pro
         35                  40                  45 gtt ctt ttt gtc aag acc gac ctg tcc ggt gcc ctg aac gaa ctg cag     192
Val Leu Phe Val Lys Thr Asp Leu Ser Gly Ala Leu Asn Glu Leu Gln
     50                  55                  60 gac gag gca gcg cgg cta tcg tgg ctg gcc acg acg ggc gtt cct tgc     240
Asp Glu Ala Ala Arg Leu Ser Trp Leu Ala Thr Thr Gly Val Pro Cys
 65                  70                  75                  80 gca gct gtg ctc gac gtt gtc act gaa gcg gga agg gac tgg ctg cta     288
Ala Ala Val Leu Asp Val Val Thr Glu Ala Gly Arg Asp Trp Leu Leu
                 85                  90                  95
```

| | | | | | | | | | | | | | | |
|---|---|---|---|---|---|---|---|---|---|---|---|---|---|---|
| ttg | ggc | gaa | gtg | ccg | ggg | cag | gat | ctc | ctg | tca | tct | cac | ctt | gct | cct | 336 |
| Leu | Gly | Glu | Val | Pro | Gly | Gln | Asp | Leu | Leu | Ser | Ser | His | Leu | Ala | Pro |
| | | | 100 | | | | | 105 | | | | | 110 | | |

```
ttg ggc gaa gtg ccg ggg cag gat ctc ctg tca tct cac ctt gct cct    336
Leu Gly Glu Val Pro Gly Gln Asp Leu Leu Ser Ser His Leu Ala Pro
            100                 105                 110 gcc gag aaa gta tcc atc ctg gct gac gca ctg cgg cgg ctg cat acg    384
Ala Glu Lys Val Ser Ile Leu Ala Asp Ala Leu Arg Arg Leu His Thr
            115                 120                 125 ctt gat ccg gct acc tgc cca ttc gac cac caa gcg aaa cat cgc atc    432
Leu Asp Pro Ala Thr Cys Pro Phe Asp His Gln Ala Lys His Arg Ile
    130                 135                 140 gag cga gca cgt act cgg ctg gaa gcc ggt ctt gtc gat cag gac gat    480
Glu Arg Ala Arg Thr Arg Leu Glu Ala Gly Leu Val Asp Gln Asp Asp
145                 150                 155                 160 ctg gac gaa gag cat cag ggg ctc gcg cca gcc gaa ctg ttc gcc agg    528
Leu Asp Glu Glu His Gln Gly Leu Ala Pro Ala Glu Leu Phe Ala Arg
                165                 170                 175 ctc aag gcg cgc ctg ccc gac ggc gac gat ctc gtc gtg acc cac ggc    576
Leu Lys Ala Arg Leu Pro Asp Gly Asp Asp Leu Val Val Thr His Gly
            180                 185                 190 gac gcc tgc ttg ccg aat atc ctg gtg gaa aac ggc cgc ttt tct gga    624
Asp Ala Cys Leu Pro Asn Ile Leu Val Glu Asn Gly Arg Phe Ser Gly
        195                 200                 205 ttc atc gac tgt ggc cgg ctg ggt gtg gcg gac cgc tat cag gac ata    672
Phe Ile Asp Cys Gly Arg Leu Gly Val Ala Asp Arg Tyr Gln Asp Ile
    210                 215                 220 gcg ttg gct acc cgt gat att gct gaa gag ctt ggc ggc gag tgg gct    720
Ala Leu Ala Thr Arg Asp Ile Ala Glu Glu Leu Gly Gly Glu Trp Ala
225                 230                 235                 240 gac cgc ttc ctc gtg ctt tac ggt atc gcc gct ccc gat tcg cag cgc    768
Asp Arg Phe Leu Val Leu Tyr Gly Ile Ala Ala Pro Asp Ser Gln Arg
                245                 250                 255 atc gcc ttc tat cgc ctt ctt gac gag ttc ttc tga                    804
Ile Ala Phe Tyr Arg Leu Leu Asp Glu Phe Phe
            260                 265
```

<210> SEQ ID NO 8
<211> LENGTH: 267
<212> TYPE: PRT
<213> ORGANISM: Artificial
<220> FEATURE:
<223> OTHER INFORMATION: Synthetic Construct

<400> SEQUENCE: 8

```
Met Gly Ser Ala Ile Glu Gln Asp Gly Leu His Ala Gly Ser Pro Ala
1               5                   10                  15

Ala Trp Val Glu Arg Leu Phe Gly Tyr Asp Trp Ala Gln Gln Thr Ile
            20                  25                  30

Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
    50                  55                  60

Asp Glu Ala Ala Arg Leu Ser Trp Leu Ala Thr Thr Gly Val Pro Cys
65                  70                  75                  80

Ala Ala Val Leu Asp Val Val Thr Glu Ala Gly Arg Asp Trp Leu Leu
                85                  90                  95

Leu Gly Glu Val Pro Gly Gln Asp Leu Leu Ser Ser His Leu Ala Pro
            100                 105                 110

Ala Glu Lys Val Ser Ile Leu Ala Asp Ala Leu Arg Arg Leu His Thr
            115                 120                 125

Leu Asp Pro Ala Thr Cys Pro Phe Asp His Gln Ala Lys His Arg Ile
    130                 135                 140
```

```
Glu Arg Ala Arg Thr Arg Leu Glu Ala Gly Leu Val Asp Gln Asp
145                 150                 155                 160

Leu Asp Glu Glu His Gln Gly Leu Ala Pro Ala Glu Leu Phe Ala Arg
            165                 170                 175

Leu Lys Ala Arg Leu Pro Asp Gly Asp Leu Val Val Thr His Gly
            180                 185                 190

Asp Ala Cys Leu Pro Asn Ile Leu Val Glu Asn Gly Arg Phe Ser Gly
        195                 200                 205

Phe Ile Asp Cys Gly Arg Leu Gly Val Ala Arg Tyr Gln Asp Ile
    210                 215                 220

Ala Leu Ala Thr Arg Asp Ile Ala Glu Glu Leu Gly Gly Glu Trp Ala
225                 230                 235                 240

Asp Arg Phe Leu Val Leu Tyr Gly Ile Ala Ala Pro Asp Ser Gln Arg
                245                 250                 255

Ile Ala Phe Tyr Arg Leu Leu Asp Glu Phe Phe
            260                 265
```

<210> SEQ ID NO 9
<211> LENGTH: 804
<212> TYPE: DNA
<213> ORGANISM: Artificial
<220> FEATURE:
<223> OTHER INFORMATION: CpG poor Neo resistance sequence
<220> FEATURE:
<221> NAME/KEY: CDS
<222> LOCATION: (1)..(804)

<400> SEQUENCE: 9

```
atg gga agt gcc att gaa caa gac gga ttg cac gca ggt tct cct gca       48
Met Gly Ser Ala Ile Glu Gln Asp Gly Leu His Ala Gly Ser Pro Ala
1               5                   10                  15 gct tgg gtg gag agg cta ttt ggc tac gac tgg gca caa cag aca ata       96
Ala Trp Val Glu Arg Leu Phe Gly Tyr Asp Trp Ala Gln Gln Thr Ile
            20                  25                  30 ggc tgc tct gac gca gca gtg ttc aga ctg tca gca cag ggg aga cca      144
Gly Cys Ser Asp Ala Ala Val Phe Arg Leu Ser Ala Gln Gly Arg Pro
        35                  40                  45 gtt ctt ttt gtc aag act gac ctg tca ggt gcc ctg aac gaa ctg cag      192
Val Leu Phe Val Lys Thr Asp Leu Ser Gly Ala Leu Asn Glu Leu Gln
    50                  55                  60 gac gag gca gca aga cta agt tgg ctg gcc act act ggt gtt cct tgt      240
Asp Glu Ala Ala Arg Leu Ser Trp Leu Ala Thr Thr Gly Val Pro Cys
65                  70                  75                  80 gca gct gtg ttg gac gtt gtc act gaa gca gga agg gac tgg ctg cta      288
Ala Ala Val Leu Asp Val Val Thr Glu Ala Gly Arg Asp Trp Leu Leu
                85                  90                  95 ttg ggt gaa gtg cct ggg cag gat ctc ctg tca tct cac ctt gct cct      336
Leu Gly Glu Val Pro Gly Gln Asp Leu Leu Ser Ser His Leu Ala Pro
            100                 105                 110 gca gag aaa gta tcc atc ctg gct gac gca ctg aga aga ctg cat act      384
Ala Glu Lys Val Ser Ile Leu Ala Asp Ala Leu Arg Arg Leu His Thr
        115                 120                 125 ctt gat cca gct acc tgc cca ttt gac cac caa gca aaa cat aga att      432
Leu Asp Pro Ala Thr Cys Pro Phe Asp His Gln Ala Lys His Arg Ile
    130                 135                 140 gag aga gca cga act aga ctg gaa gca ggt ctt gta gat cag gac gat      480
Glu Arg Ala Arg Thr Arg Leu Glu Ala Gly Leu Val Asp Gln Asp Asp
145                 150                 155                 160 ctg gac gaa gag cat cag ggg ttg gca cca gca gaa ctg ttt gcc agg      528
Leu Asp Glu Glu His Gln Gly Leu Ala Pro Ala Glu Leu Phe Ala Arg
```

```
                           165                 170                 175
ctc aag gca aga ctg cct gac ggt gaa gat ttg gtt gtg acc cac ggt    576
Leu Lys Ala Arg Leu Pro Asp Gly Glu Asp Leu Val Val Thr His Gly
            180                 185                 190 gac gcc tgc ttg cct aat atc ctg gtg gaa aac ggc aga ttt tct gga    624
Asp Ala Cys Leu Pro Asn Ile Leu Val Glu Asn Gly Arg Phe Ser Gly
        195                 200                 205 ttc att gac tgt ggc aga ctg ggt gtg gca gac aga tat cag gac ata    672
Phe Ile Asp Cys Gly Arg Leu Gly Val Ala Asp Arg Tyr Gln Asp Ile
    210                 215                 220 gca ttg gct acc aga gat att gct gaa gag ctt ggt ggt gag tgg gct    720
Ala Leu Ala Thr Arg Asp Ile Ala Glu Glu Leu Gly Gly Glu Trp Ala
225                 230                 235                 240 gac aga ttc ttg gtg ctt tac ggt ata gcc gct cct gat tca cag aga    768
Asp Arg Phe Leu Val Leu Tyr Gly Ile Ala Ala Pro Asp Ser Gln Arg
                245                 250                 255 ata gcc ttc tat aga ctt ctt gac gag ttc ttc tga                    804
Ile Ala Phe Tyr Arg Leu Leu Asp Glu Phe Phe
            260                 265

<210> SEQ ID NO 10
<211> LENGTH: 267
<212> TYPE: PRT
<213> ORGANISM: Artificial
<220> FEATURE:
<223> OTHER INFORMATION: Synthetic Construct

<400> SEQUENCE: 10

Met Gly Ser Ala Ile Glu Gln Asp Gly Leu His Ala Gly Ser Pro Ala
1               5                   10                  15

Ala Trp Val Glu Arg Leu Phe Gly Tyr Asp Trp Ala Gln Gln Thr Ile
            20                  25                  30

Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
    50                  55                  60

Asp Glu Ala Ala Arg Leu Ser Trp Leu Ala Thr Thr Gly Val Pro Cys
65                  70                  75                  80

Ala Ala Val Leu Asp Val Val Thr Glu Ala Gly Arg Asp Trp Leu Leu
                85                  90                  95

Leu Gly Glu Val Pro Gly Gln Asp Leu Leu Ser Ser His Leu Ala Pro
            100                 105                 110

Ala Glu Lys Val Ser Ile Leu Ala Asp Ala Leu Arg Arg Leu His Thr
        115                 120                 125

Leu Asp Pro Ala Thr Cys Pro Phe Asp His Gln Ala Lys His Arg Ile
    130                 135                 140

Glu Arg Ala Arg Thr Arg Leu Glu Ala Gly Leu Val Asp Gln Asp Asp
145                 150                 155                 160

Leu Asp Glu Glu His Gln Gly Leu Ala Pro Ala Glu Leu Phe Ala Arg
                165                 170                 175

Leu Lys Ala Arg Leu Pro Asp Gly Glu Asp Leu Val Val Thr His Gly
            180                 185                 190

Asp Ala Cys Leu Pro Asn Ile Leu Val Glu Asn Gly Arg Phe Ser Gly
        195                 200                 205
```

-continued

```
Phe Ile Asp Cys Gly Arg Leu Gly Val Ala Asp Arg Tyr Gln Asp Ile
    210             215             220

Ala Leu Ala Thr Arg Asp Ile Ala Glu Glu Leu Gly Gly Glu Trp Ala
225             230             235             240

Asp Arg Phe Leu Val Leu Tyr Gly Ile Ala Ala Pro Asp Ser Gln Arg
            245             250             255

Ile Ala Phe Tyr Arg Leu Leu Asp Glu Phe Phe
            260             265
```